US010687898B2

(12) United States Patent
Trayanova et al.

(10) Patent No.: US 10,687,898 B2
(45) Date of Patent: Jun. 23, 2020

(54) SYSTEMS AND METHODS FOR ATRIAL FIBRILLATION TREATMENT AND RISK ASSESSMENT

(71) Applicant: The Johns Hopkins University, Baltimore, MD (US)

(72) Inventors: Natalia A. Trayanova, Baltimore, MD (US); Patrick M. Boyle, Baltimore, MD (US); Sohail Zahid, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 166 days.

(21) Appl. No.: 15/526,199

(22) PCT Filed: Nov. 5, 2015

(86) PCT No.: PCT/US2015/059298
§ 371 (c)(1),
(2) Date: May 11, 2017

(87) PCT Pub. No.: WO2016/077154
PCT Pub. Date: May 19, 2016

(65) Prior Publication Data
US 2017/0319278 A1    Nov. 9, 2017

Related U.S. Application Data

(60) Provisional application No. 62/079,986, filed on Nov. 14, 2014.

(51) Int. Cl.
G06K 9/00    (2006.01)
A61B 34/10   (2016.01)
(Continued)

(52) U.S. Cl.
CPC .............. *A61B 34/10* (2016.02); *A61B 5/055* (2013.01); *A61B 5/7275* (2013.01); *A61B 6/032* (2013.01);
(Continued)

(58) Field of Classification Search
None
See application file for complete search history.

(56) References Cited

U.S. PATENT DOCUMENTS 9,877,789 B2 *   1/2018   Ghosh .................. A61N 1/0484
2009/0099563 A1 * 4/2009   Ciaccio ................ A61B 5/1075
                                                    606/41
(Continued)

FOREIGN PATENT DOCUMENTS

EP        1750215 A1       2/2007
WO   WO-2013-066895 A1     5/2013

OTHER PUBLICATIONS

International Search Report and Written Opinion in International Application No. PCT/US2015/059298, dated Feb. 17, 2016.
(Continued)

Primary Examiner — Shervin K Nakhjavan
(74) Attorney, Agent, or Firm — Venable LLP; Henry J. Daley

(57) ABSTRACT

According to some embodiments of the invention, a method for providing an atrial fibrillation (AF) ablation treatment plan includes receiving imaging data for at least a portion of an atrial region of a subject's heart, and processing the imaging data to characterize tissue as one of fibrotic tissue or non-fibrotic tissue. The method further includes calculating a metric of spatial distribution of at least a portion of the tissue characterized as fibrotic tissue from the processing the imaging data, identifying a cardiac tissue ablation target based on the metric, and providing an AF treatment plan that
(Continued)

includes the cardiac tissue ablation target as at least a portion of the AF treatment plan.

18 Claims, 16 Drawing Sheets
(15 of 16 Drawing Sheet(s) Filed in Color)

(51) Int. Cl.
    *A61B 5/055*     (2006.01)
    *A61B 5/00*     (2006.01)
    *A61B 6/03*     (2006.01)
    *A61B 6/00*     (2006.01)
    *A61B 18/00*     (2006.01)
    *A61B 18/14*     (2006.01)

(52) U.S. Cl.
    CPC ............ *A61B 6/037* (2013.01); *A61B 6/5217* (2013.01); *A61B 18/1492* (2013.01); *A61B 2018/00351* (2013.01); *A61B 2018/00357* (2013.01); *A61B 2018/00363* (2013.01); *A61B 2018/00577* (2013.01); *A61B 2034/104* (2016.02); *A61B 2034/105* (2016.02)

(56) References Cited

U.S. PATENT DOCUMENTS

| | | | |
|---|---|---|---|
| 2010/0160765 A1 | 6/2010 | Marrouche et al. | |
| 2010/0298694 A1* | 11/2010 | Marrouche | G06T 7/0012 600/420 |
| 2011/0230775 A1* | 9/2011 | Barley | A61B 5/02007 600/508 |
| 2011/0264000 A1* | 10/2011 | Paul | A61B 5/0537 600/547 |
| 2013/0197881 A1* | 8/2013 | Mansi | A61N 1/3627 703/2 |
| 2014/0022250 A1* | 1/2014 | Mansi | G06T 19/20 345/420 |
| 2014/0023256 A1* | 1/2014 | Nazarian | A61B 5/7203 382/131 |
| 2014/0142422 A1* | 5/2014 | Manzke | A61B 8/0841 600/424 |
| 2014/0330134 A1 | 11/2014 | Chon et al. | |
| 2015/0042646 A1* | 2/2015 | Connaniciu | G06T 17/20 345/420 |
| 2015/0099979 A1* | 4/2015 | Caves | A61B 5/0044 600/475 |
| 2018/0240234 A1* | 8/2018 | Marrouche | G06T 7/0012 |

OTHER PUBLICATIONS

Daccarett et al., "MRI of the left atrium: predicting clinical outcomes in patients with atrial fibrillation," Expert Review of Cardiovascular Therapy, vol. 9, Issue 1, pp. 105-111 (2011).

* cited by examiner

| Category | Parameter(s) | Value |
|---|---|---|
| Geometry | Average Number of Vertices | 1638120.38 |
| | Average Number of Elements | 1812802.61 |
| | Average Edge Length (μm) | 464.39 |
| Monodomain conductivity (mS/mm) | Longitudinal ($\bullet$ L, non-fibrotic) | 0.1264 |
| | Longitudinal ($\bullet$ L, fibrotic) | 0.0546 |
| | Transverse ($\bullet$ T, non-fibrotic) | 0.0252 |
| | Transverse ($\bullet$ T, fibrotic) | 0.0068 |
| | Normal ($\bullet$ N, non-fibrotic) | 0.0252 |
| | Normal ($\bullet$ N, fibrotic) | 0.0068 |
| Computation | Number of Intel X5660 CPUS at 2.8 GHz | 24 |
| | Wall time to Simulate 1 Second (min) | 47.33 |

FIG. 2

◯Rapid pacing sites

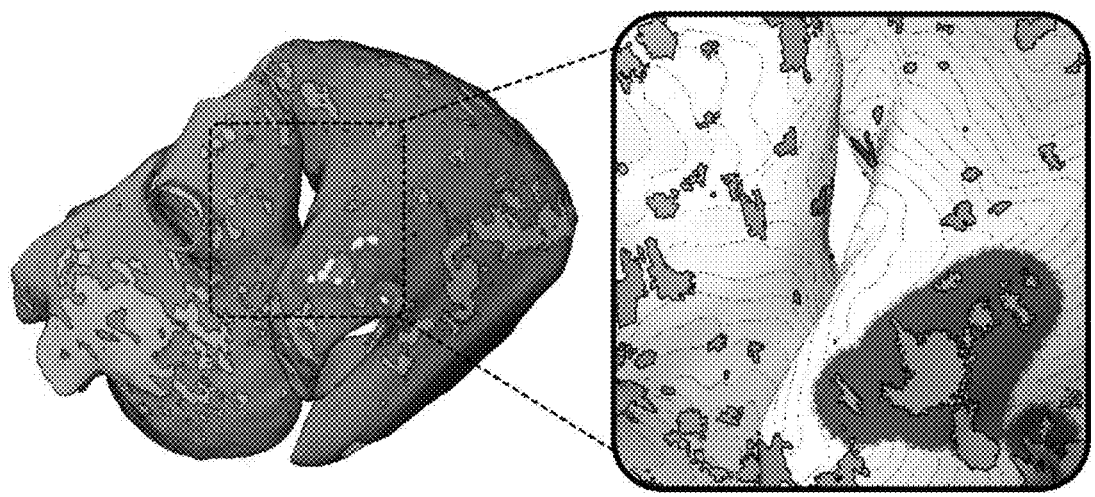
FIG. 17
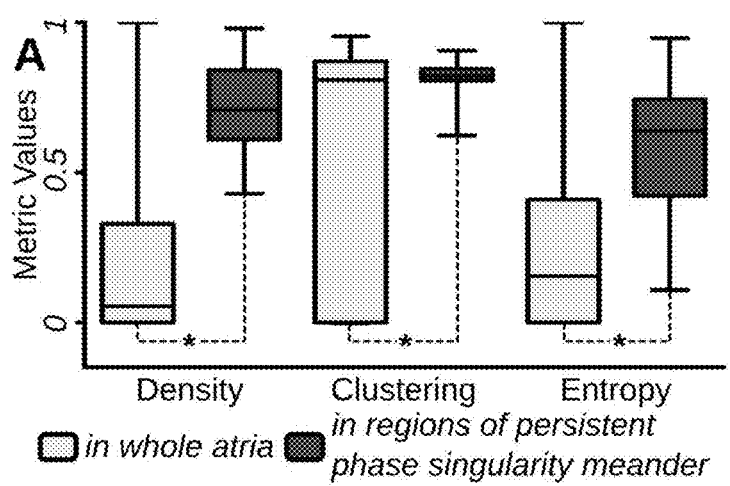
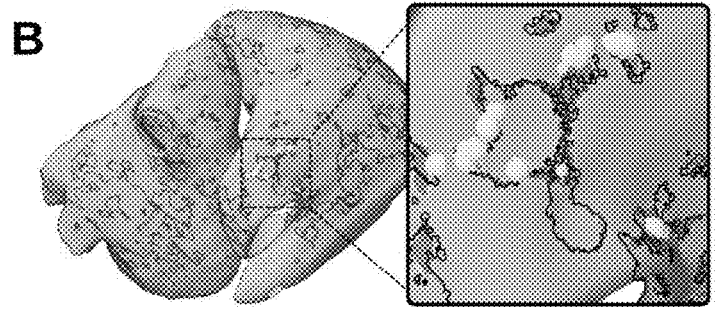
FIG. 18A, 18B

SYSTEMS AND METHODS FOR ATRIAL FIBRILLATION TREATMENT AND RISK ASSESSMENT

This application is a U.S. National Phase Application under 35 U.S.C. § 371 of PCT/US2015/059298 filed Nov. 5, 2015, the entire content of which is hereby incorporated by reference and this application claims priority to U.S. Provisional Application No. 62/079,986, filed Nov. 14, 2014, the entire content of which is hereby incorporated by reference.

This invention was made with Government support under Grant No. DP1-HL123271 from the Department of Health and Human Services, The National Institutes of Health (NIH), and under Grant No. CDI 1124804 from the National Science Foundation. The U.S. Government has certain rights in this invention.

BACKGROUND

1. Technical Field

The field of the currently claimed embodiments of this invention relates to systems and methods for atrial fibrillation treatment and/or related risk assessment, and more particularly systems and methods for atrial fibrillation treatment and/or related risk assessment using at least one metric of complexity of spatial distribution of tissue characterized as fibrotic tissue.

2. Discussion of Related Art

Catheter-based ablation to terminate atrial fibrillation (AF) is effective in some cases but outcomes are poor in patients with persistent AF and structural remodeling of the atria, including extensive fibrosis, which perpetuates AF. Current ablation procedures relying on electro-anatomical mapping to determine the ablation targets in patients with persistent AF and fibrotic remodeling in the atria are ineffective, invasive, and time-consuming. The state-of-the-art approach for identifying these targets is electro-anatomical mapping at the time of treatment, which is an invasive, tedious, and time-consuming procedure.

In addition, late gadolinium enhancement magnetic resonance imaging (LGE-MRI) is currently used in some clinical settings to quantify the amount of fibrosis in each patient to determine whether he/she is an appropriate candidate for catheter ablation. Currently, only the observed amount of fibrosis is used in attempts to make atrial fibrosis-related risk assessments. There thus remains a need for improved systems and methods for atrial fibrillation treatment and/or related risk assessment.

SUMMARY

According to some embodiments of the invention, a method for providing an atrial fibrillation (AF) ablation treatment plan includes receiving imaging data for at least a portion of an atrial region of a subject's heart, and processing the imaging data to characterize tissue as one of fibrotic tissue or non-fibrotic tissue. The method further includes calculating a metric of spatial distribution of at least a portion of the tissue characterized as fibrotic tissue from the processing the imaging data, identifying a cardiac tissue ablation target based on the metric, and providing an AF treatment plan that includes the cardiac tissue ablation target as at least a portion of the AF treatment plan.

According to some embodiments of the invention, receiving imaging data is receiving at least one of MRI, CT or PET imaging data. According to some embodiments, receiving imaging data is receiving late gadolinium enhancement magnetic resonance (LGE-MRI) data. According to some embodiments, the method further includes identifying a plurality of cardiac tissue ablation targets based on the metric, wherein the AF treatment plan further includes the plurality of cardiac tissue ablation targets. According to some embodiments, the method further includes calculating a plurality of metrics of spatial distribution of tissue characterized as fibrotic tissue from the processing the imaging data. The metric of spatial distribution can be calculated for each of a plurality of subvolumes of the atrial regions of the subject's heart. According to some embodiments, the plurality of subvolumes are between 0.5 mm and 10 mm in radius. According to some embodiments, the plurality of subvolumes are between 0.5 mm and 3 mm in radius. According to some embodiments, the plurality of subvolumes are between 1.3 mm and 1.7 mm in radius.

According to some embodiments of the invention, the plurality of metrics include at least density, clustering and complexity metrics. According to some embodiments, calculating a metric includes calculating the metric for a portion of the tissue characterized as fibrotic tissue having a degree of fibrosis that falls within a predetermined range.

According to some embodiments of the invention, a method for providing a risk assessment for atrial fibrillation (AF) and related health risks, as well as recurrence of atrial arrhythmia after ablation, includes receiving imaging data for at least a portion of an atrial region of a subject's heart, and processing the imaging data to characterize tissue as one of fibrotic tissue or non-fibrotic tissue. The method further includes calculating a metric of spatial distribution of at least a portion of the tissue characterized as fibrotic tissue from the processing the imaging data for a plurality of localized regions within the portion of the atrial region of the subject's heart. The method further includes identifying a risk of at least one of developing atrial fibrillation, worsening atrial fibrillation, recurrence of atrial arrhythmias and fibrillation after ablation treatment, heart failure, or stroke based the metric of spatial distribution calculated for the plurality of localized regions.

According to some embodiments of the invention, a non-transitory computer-readable medium includes computer-executable code for providing an atrial fibrillation (AF) ablation treatment plan, the computer-executable code including instructions that, when executed by the computer, cause the computer to receive imaging data for at least a portion of an atrial region of a subject's heart, process the imaging data to characterize tissue as one of fibrotic tissue or non-fibrotic tissue, and calculate a metric of spatial distribution of at least a portion of the tissue characterized as fibrotic tissue from the processing the imaging data. The instructions further cause the computer to identify a cardiac tissue ablation target based on the metric, and provide an AF treatment plan that includes the cardiac tissue ablation target as at least a portion of the AF treatment plan.

According to some embodiments of the invention, a non-transitory computer-readable medium including computer-executable code for providing a risk assessment for atrial fibrillation (AF) and related health risks, as well as recurrence of atrial arrhythmia after ablation when executed by the computer, causes the computer to receive imaging data for at least a portion of an atrial region of a subject's heart, process the imaging data to characterize tissue as one of fibrotic tissue or non-fibrotic tissue, and calculate a metric of spatial distribution of at least a portion of the tissue characterized as fibrotic tissue from the processing the imaging data for a plurality of localized regions within the portion of the atrial region of the subject's heart. The computer-executable code further causes the computer to identify a risk of at least one of developing atrial fibrillation, worsening atrial fibrillation, recurrence of atrial arrhythmias and fibrillation after ablation treatment, heart failure, or stroke based the metric of spatial distribution calculated for the plurality of localized regions.

According to some embodiments of the invention, a medical imaging system includes a data processor configured to receive imaging data for at least a portion of an atrial region of a subject's heart, process the imaging data to characterize tissue as one of fibrotic tissue or non-fibrotic tissue, and calculate a metric of spatial distribution of at least a portion of the tissue characterized as fibrotic tissue from the processing the imaging data for a plurality of localized regions within the portion of the atrial region of the subject's heart. The data processor is further configured to provide at least one of a map based on the metric, at least one ablation target based on the metric, or a risk assessment for at least one of developing atrial fibrillation, worsening atrial fibrillation, recurrent atrial fibrillation, heart failure, or stroke based the metric.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of the description, drawings, and examples.

FIG. 2 shows a table listing mesh characteristics, electrophysiological parameters, and simulation times;

FIG. 17 shows simulated ablation (purple) of the confined region within which persistent phase singularities (gold) meandered;

FIG. 18A shows spatial metrics of fibrosis distribution were higher within regions of persistent phase singularity dynamic locations than in the atria as a whole (*=p<0.01);

FIG. 18B shows a map of regions where all metric values were >0.6 (red), dynamic locations of persistent phase singularities (gold), and fibrosis (black);

DETAILED DESCRIPTION

Figure 1:
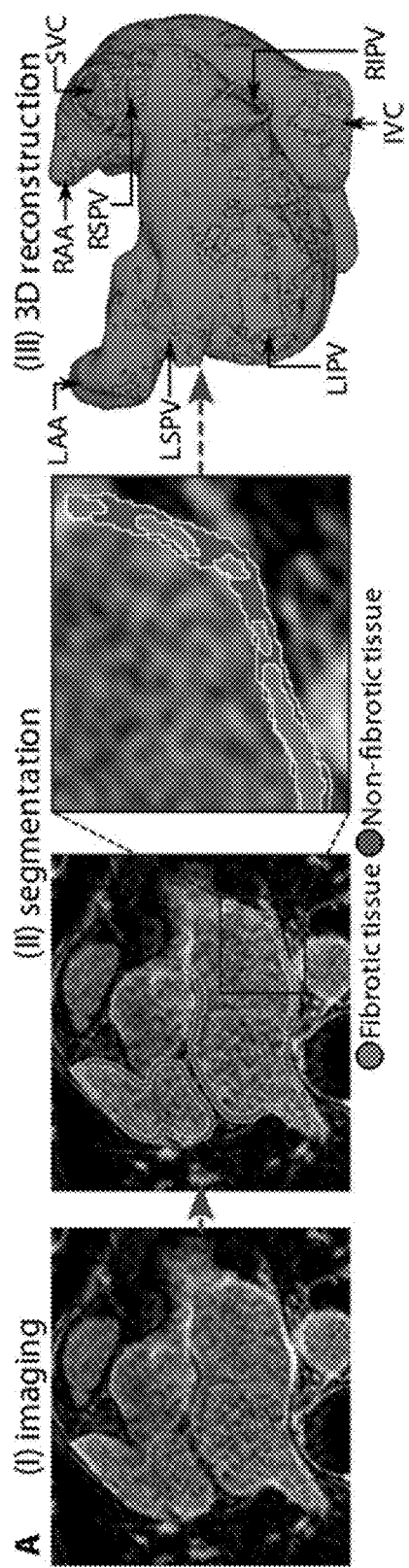
FIG. 1 is a schematic illustration of a model generation pipeline used to construct image-based models of the fibrotic human atria.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to a novel technique to identify optimal ablation targets in AF patients with fibrosis. The term "fibrosis" is intended to have a broad meaning to include atrial tissue regions that have become remodeled, unhealthy, fibrotic, and/or scarred due to aging, genetic predisposition, or disease (e.g., atrial fibrosis, electrically-remodeled tissue, etc.) The term "fibrosis" is intended to be synonymous with the terms scarring or remodeled, for example. When the term "fibrosis" or fibrotic tissue is used herein, it is considered synonymous with the term unhealthy tissue. The term "fibrotic tissue" can indicate tissue having varying degrees of fibrosis. For example, fibrotic tissue can indicate any tissue having some degree of fibrosis. This can include tissue with a very small degree of fibrosis, as well as tissue with a very large degree of fibrosis. The term fibrotic tissue can also indicate tissue having at least a predetermined degree of fibrosis, or a degree of fibrosis that falls within a predetermined range. The degree of fibrosis may be determined using a variety of methods. According to some embodiments, LGE-MRI is used to distinguish fibrotic and non-fibrotic tissue. LGE-MRI can also be used to determine a degree of fibrosis of the fibrotic tissue. However, the embodiments of the present invention are not limited to LGR-MRI.

The term "ablation" is intended to have a broad definition that can include RF ablation, thermal ablation, laser ablation, surgical ablation, cryoablation, and photodynamic therapy, for example. Given unique 3D reconstructions of atrial fibrosis distributions for each patient (obtained via clinical imaging), our approach according to some embodiments is to apply a series of spatial analysis steps of the patient-specific spatial distribution of fibrosis to produce personalized maps of locations where remodeling promotes AF perpetuation. This can also be termed as mapping regions of healthy and unhealthy tissue. These locations constitute optimal catheter ablation targets. (The term "optimal does not mean that they must be the absolute best. There is always a degree of tolerance for deviations from the exact optimum.) In other embodiments, the number and/or cumulative area of such locations can be used to provide risk assessments for AF-related conditions. In some embodiments, it can be useful to use thresholds to provide a binary assessment of risk. Some of the risks that can be assessed according to some embodiments of the current invention can include, but are not limited to, one or more of a risk of developing atrial fibrillation, a risk of existing atrial fibrillation becoming worse, a risk of atrial arrhythmias and fibrillation recurrence following attempted treatment, a risk of heart failure, and a risk of atrial fibrillation-associated stroke.

As mention above, late gadolinium enhancement magnetic resonance imaging (LGE-MRI) is currently used in some clinical settings to quantify the amount of fibrosis in each patient to determine whether he/she is an appropriate candidate for catheter ablation. LGE-MRI images can be used to reconstruct 3D representations of patient-specific atrial fibrosis patterns according to an embodiment of the current invention. Some embodiments of the current invention leverage these representations to create a novel paradigm for persistent AF ablation treatment planning. According to such embodiments, we analyze the specific spatial characteristics of fibrotic tissue regions in each patient to noninvasively pinpoint the personalized set of possible ablation targets.

The state-of-the-art approach for identifying these targets is electro-anatomical mapping at the time of treatment, which is an invasive, tedious, and time-consuming procedure. Some embodiments of the current invention can guide electroanatomical mapping or eliminate it altogether since our analysis of images acquired from each patient reveals the specific locations where the distribution of fibrosis creates most favorable conditions for AF perpetuation. Furthermore, under the new paradigm enabled by embodiments of the invention, the identification process of possible targets can be conducted before the invasive part of the procedure by analyzing patient-specific fibrosis patterns acquired from noninvasive pre-procedure imaging (e.g., LGE-MRI). Should the invasive procedure fail, the above-described approach can also be utilized to assess risk of post-ablation recurrence of AF. Thus, in addition to improving treatment efficacy, our approach can lead to shorter, simpler clinical procedures.

Some embodiments of the current invention provide a quick and simple method to identify a set of potential AF ablation targets, in real time, by analyzing the personalized spatial distribution of atrial fibrosis to determine its complexity. Further non-invasive narrowing down of the ablation targets to an optimal set, if desired, could be done by conducting an off-line set of computer simulations as described in U.S. application Ser. No. 14/094,334 assigned to the same Assignee as the current application, the entire content of which is incorporated herein by reference.

A computing device may perform certain functions in response to processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device such as an MRI scanner, for example.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

The following examples describe some embodiments in more detail. The broad concepts of the current invention are not intended to be limited to the particular examples. Further, concepts from each example are not limited to that example, but may be combined with other embodiments of the system.

EXAMPLES

Example 1: Patient-Specific Models Link Reentrant Driver Localization in Atrial Fibrillation to Fibrosis Spatial Pattern Atrial fibrillation (AF) is the most common cardiac arrhythmia and a major contributor to mortality and morbidity, affecting 1-2% of the worldwide population. [1] Over the past decade, catheter ablation has emerged as a potential approach to treat AF; however, the efficacy of this procedure remains limited, with a particularly low success rate (~50%) in patients with persistent AF (PsAF). [2] Treatment of this disease is further encumbered by its progressive nature—each year, at least 5% of patients with less severe forms of AF develop PsAF. [3]

Evidence from recent clinical and experimental studies suggests that PsAF might be maintained by reentrant drivers (RDs) (i.e., rotors), but the mechanisms linking RD formation and PsAF perpetuation remain unknown. [4-6] A large number of patients with PsAF have extensive atrial structural remodeling, especially fibrosis [7-9] which can lead to slow propagation, reduced excitability, and unidirectional block, [10, 11] and thus to the establishment of an arrhythmogenic atrial substrate and increased likelihood of RD formation. [12-15] Since the spatial patterns of atrial fibrosis are complex and vary widely between individuals [8, 9] the precise mechanistic link between the substrate fibrotic remodeling and RDs in patients with PsAF remains elusive. Better understanding of this relationship will increase the understanding of PsAF pathophysiology and help pave the way towards personalized anti-arrhythmia treatment planning.

A personalized computer simulation approach based on atrial fibrosis characterization is used to show that AF induced by programmed stimulation in the fibrotic substrate is perpetuated by RDs persisting in regions with specific fibrosis spatial patterns. We developed 20 patient-specific three-dimensional (3D) atrial models that incorporated individualized representations of fibrosis derived from late-gadolinium enhanced magnetic resonance (LGE-MRI) scans. Simulations of programmed electrical stimulation were then used to determine how the locations where the organizing centers of RDs (i.e., phase singularities; RD-PSs) were induced and persisted relate quantitatively to the fibrosis spatial patterns. We provide unique insight into the potential role of the fibrotic substrate in PsAF dynamics.

Methods

Patient Population

From June 2013 to October 2014, 20 patients who had PsAF (uninterrupted AF lasting longer than 7 days) were enrolled in this study. Patients who had contra-indications to MRI, history of prior catheter ablation or atrial surgery, or intra-cardiac thrombi observed during trans-esophageal echocardiography were excluded. This study was approved by the Institutional Ethics Committee at the University of Bordeaux, and all patients gave informed consent. This investigation conformed to the principles outlined in the Declaration of Helsinki.

Reconstruction of 3D Patient-Specific Atrial Models from LGE-MRI

Cardiac magnetic resonance was performed on a 1.5 T scanner (Magnetom Avanto, Siemens Medical Systems, Erlangen, Germany) equipped with a 32 channel cardiac coil. LGE-MRI was performed 15 min after the administration of gadolinium chelates using a 3D, ECG-gated, respiratory-navigated, and inversion recovery-prepared Turbo Fast Low Angle Shot sequence with fat saturation (voxel size: 1.25×1.25×2.5 mm$^3$). [8] In the resulting images, the biatrial wall was manually contoured and LGE and non-LGE regions were segmented using an adaptive histogram thresholding algorithm as described previously, [8] implemented in MUSIC software (LIRYC Institute, University of Bordeaux, Inria Sophia-Antipolis, France). LGE segmentation was blinded to clinical characteristics and results from computer simulations. The fibrosis burden derived from LGE segmentation was expressed as a percentage of the atrial wall. LA fibrosis burden was categorized according to Utah staging, as described previously. [7] Segmented images were up-sampled to an isotropic voxel size of 400 µm$^3$ using shape-based interpolation, [16] and 3D finite element meshes were generated from the resulting high-resolution data sets using a previously-developed approach. [17] In each patient-specific model, myocardial fiber orientations were assigned using a rule-based method. [18] A detailed description of the geometrical model construction methodology can be found in prior publications. [19-21]

Figure 3:
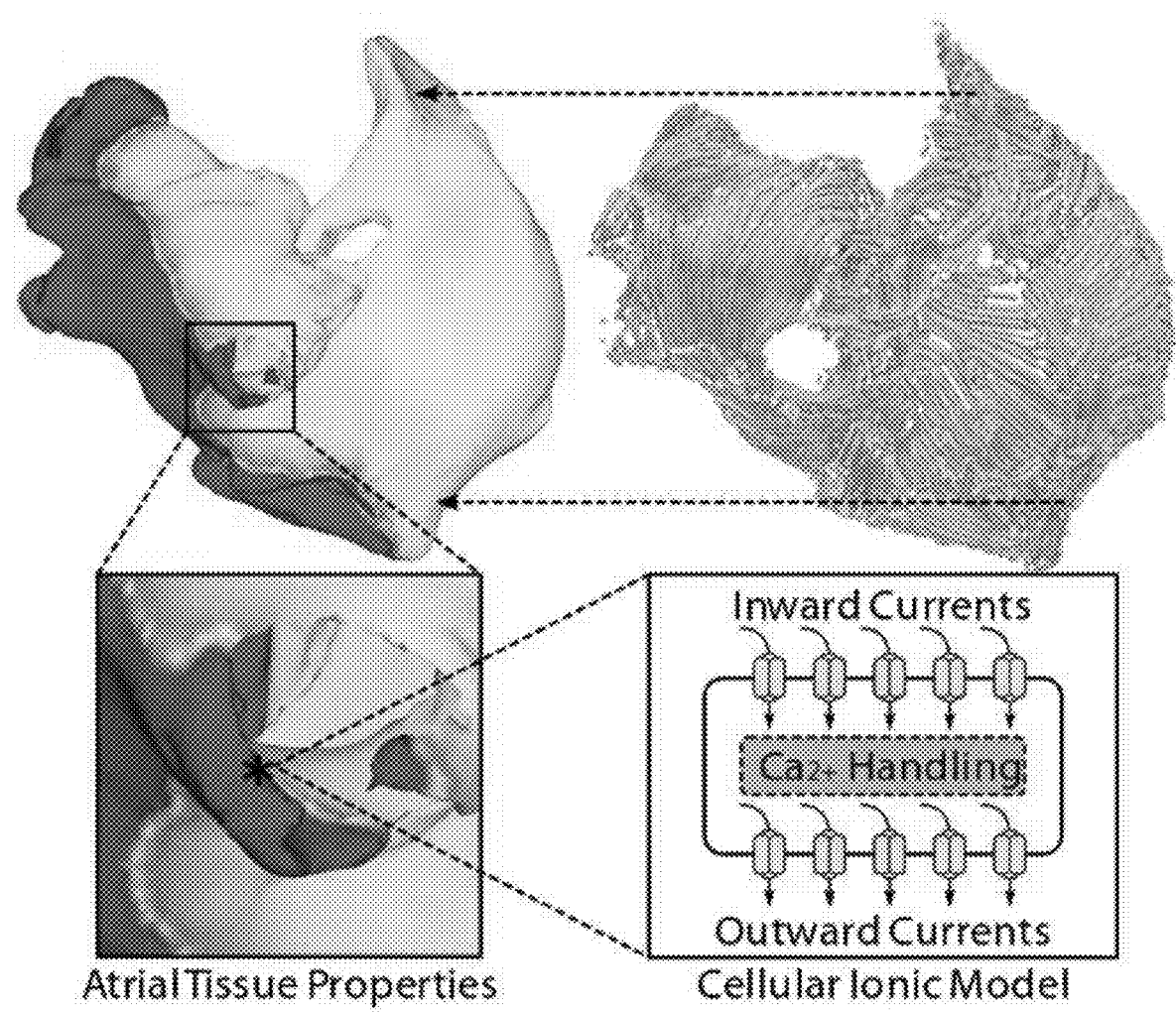
FIG. 3 is a schematic of multi-scale framework for atrial cardiac electrophysiology modeling.

Image processing and model generation are illustrated in FIG. 1. FIG. 1 shows the pipeline used to construct image-based models of the fibrotic human atria. (i): Representative LGE-MRI slice of the human atria. (ii): Segmentation of atrial tissue into fibrotic (green) and non-fibrotic (grey) regions based on voxel intensity, as described in Methods. (iii): 3D reconstruction of atrial geometry with anatomical features labelled (RIPV/RSPV/LIPV/LSPV=right/left inferior/superior pulmonary veins; LAA=left atrial appendage; IVC/SVC=inferior/superior vena cava). Details on mesh characteristics, electrophysiological parameters, and simulation times are provided in the table in FIG. 2. FIG. 3 shows a schematic of multi-scale framework for cardiac electrophysiology modeling. Electrical coupling of atrial cells at the tissue scale mediates propagation of bioelectric impulses, which originate at membrane level (action potentials in the cellular ionic model). Atrial fibre orientations, shown in the top right image, govern the preferential direction of electrical propagation.

Modeling of Atrial Electrophysiology in Fibrotic and Non-Fibrotic Regions

Figure 4:
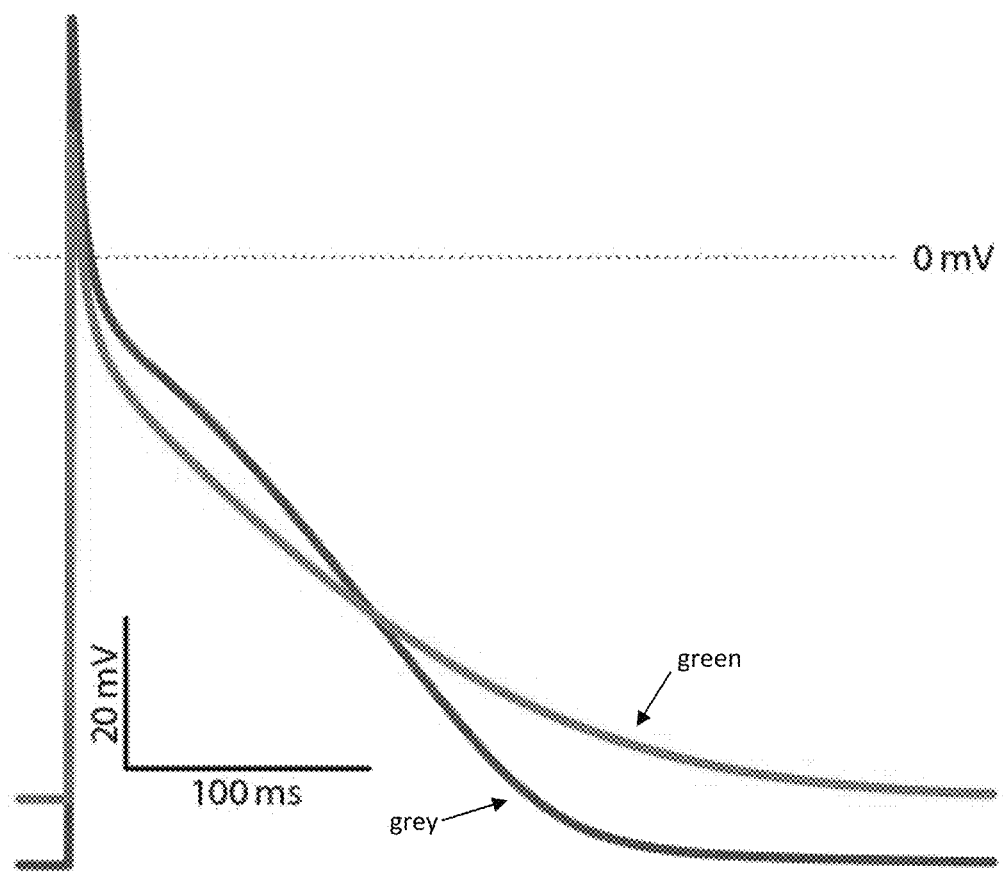
FIG. 4 shows simulated atrial action potentials in fibrotic (green) and non-fibrotic tissue (grey)

Myocyte membrane kinetics in non-fibrotic regions were represented with a human atrial action potential model under chronic AF conditions [22] modified [23] to fit intracardiac electrophysiological data (FIG. 4, grey). At the tissue level, conductivity values were assigned so that an effective longitudinal conduction velocity of 43.39 cm/s was achieved in the non-fibrotic myocardium, which was within the range of values recorded in patients with AF. [24]

Fibrotic regions were represented with remodeled electrophysiology, anisotropy, and conduction properties. The chronic AF action potential model was modified as follows to account for electrophysiological changes due to fibrotic remodeling [25-27]: 50% reduction in inward rectifier potassium current [$I_{K1}$]; 50% reduction in L-type calcium current Wad; and 40% reduction in sodium current [$I_{Na}$]. These ionic current modifications were consistent with changes in atrial myocytes subjected to elevated transforming growth factor β1, a key component of the fibrogenic signaling pathway. [28, 29] The resulting changes to the action potential (+15.4% AP duration; −7.18% resting transmembrane voltage [$V_m$]; −49.6% upstroke velocity) were consistent with those documented in fibrotic myocardium in vitro [30] (FIG. 4, green). Conductivity values in fibrotic regions were reduced by 30% to represent decreased intercellular coupling due to replacement fibrosis, collagen deposition (interstitial fibrosis), and gap junction remodeling. [12, 13] Since fibrosis results in greater conduction velocity impairment in the direction transverse to cardiac fibers, the conductivity values were further modified to achieve a longitudinal-transverse anisotropy ratio of 8:1. [12, 13] All relevant cell- and tissue-scale model parameters are provided in table in FIG. 2.

Simulation Protocol

Figure 5:
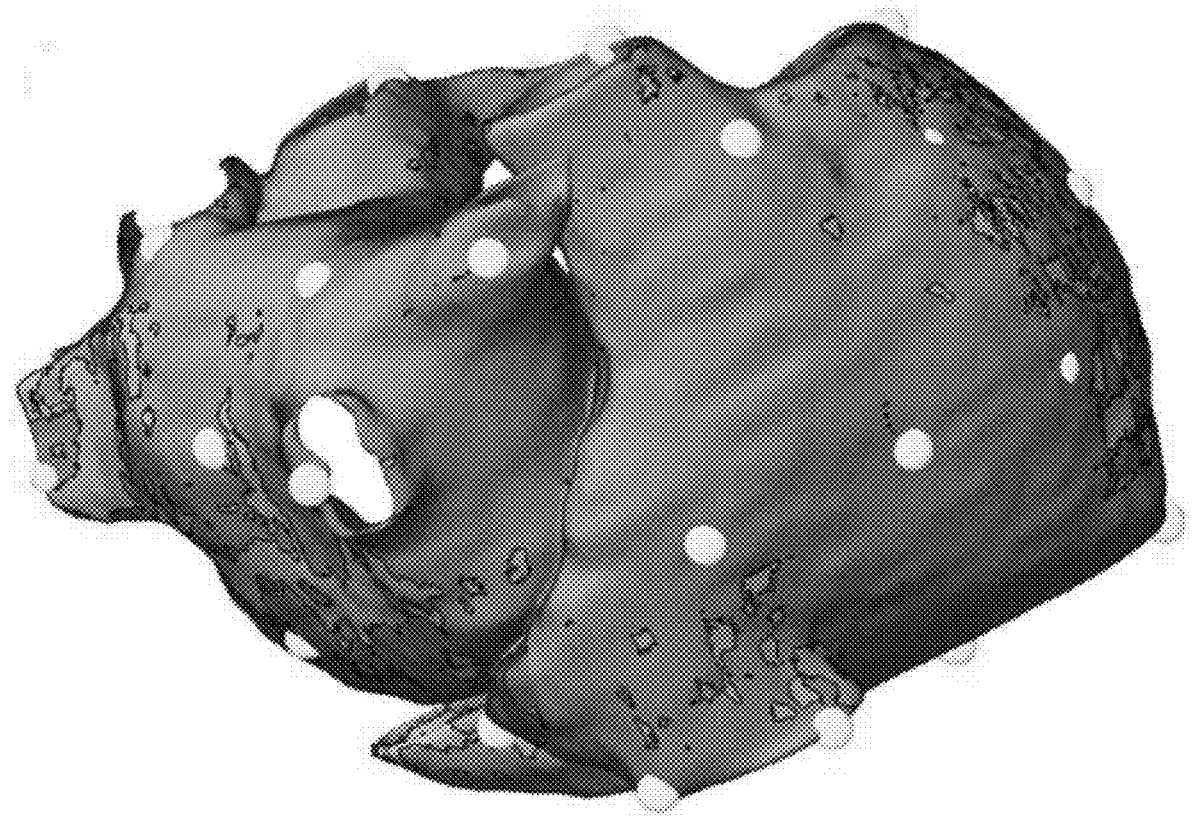
FIG. 5 illustrates locations of 30 sites where rapid pacing was applied for patient model #3.

Electrical wave propagation was governed by the monodomain formulation, and finite-element simulations were executed with the CARP software package (Johns Hopkins University and University of Bordeaux); numerical detail can be found in previous publications. [31, 32] In each patient-specific model, 30 pacing sites were distributed uniformly throughout the atria (FIG. 5). At each pacing site, a clinically relevant programmed electrical stimulation pacing sequence [33] of 14 stimulation pulses with cycle lengths decreasing from 300 ms to 150 ms in 25 ms intervals was applied in order to induce AF and assess the arrhythmogenic propensity of the fibrotic substrate. For each of the 20 patient-specific models, we simulated 30 AF induction protocols (1 for each pacing site). A patient model was categorized as inducible for AF if at least 2.5 s of self-sustained AF was observed after the last pacing stimulus.

Analysis of Arrhythmia Dynamics and Identification of Reentrant Drivers

Phase singularities were identified throughout the patient atria via phase-space analysis during a one second interval of AF; this involved converting transmembrane potential ($V_m$) maps into action potential phase maps and identifying points around which the line integral of the phase was equal to ±2π. [34] An unsupervised density-based spatial clustering algorithm [35] was then used to spatio-temporally cluster all phase singularities. If a cluster persisted throughout the entire analysis interval, the corresponding phase singularities were defined to be associated with an RD. Clusters of phase singularities that did not persist throughout the entire analysis interval were categorized as transient. In all cases, RDs had at least two rotations and lasted at least 200 ms, which is consistent with the definition of RDs in previous publications. [5, 33] In addition, for each RD, the dynamic locations of its phase singularity (RD-PS) were tracked to compute RD-PS trajectory length. Pseudo-electrograms in AF were reconstructed by differencing extracellular potential signals recovered from points 4 cm away from the right and left atrial appendages.

Quantitative Characterization of Fibrosis Spatial Pattern

To quantitatively characterize the fibrosis spatial pattern in each patient-specific atrial model, we constructed 3D maps of fibrosis density (FD) and fibrosis entropy (FE). According to some embodiments of the invention, fibrosis entropy synonymous with fibrosis complexity. FD and FE values at each location in each atrial model were calculated based on the corresponding characteristics of the local tissue element as well as on those of the surrounding tissue elements within a 2.5 mm-radius, which corresponds to the maximum distance between two adjacent voxels in the LGE-MRI scans. The local FD value was calculated as the proportion of fibrotic elements among all elements within the surrounding sub-volume. The local FE in the $i^{th}$ element was calculated as the level of disorganization within the surrounding sub-volume, quantified via Shannon entropy:

$$FE = \sum_{i=1}^{N} \frac{-p_i \ln(p_i)}{N}. \quad (1)$$

N was the number of elements within the sub-volume surrounding the $i^{th}$ element. $p_i$ was the fraction of elements neighboring the $i^{th}$ element that was a different tissue type than the $i^{th}$ element. For example, in the case of a non-fibrotic element with three out of four fibrotic neighboring elements, the value of $p_i$ was 0.75.

Statistical Analysis

Continuous variables are expressed as mean±SD. Categorical variables are expressed as percentages. Continuous variables were compared using independent-sample non-parametric tests (Wilcoxon Signed-Rank tests). Relationships between continuous variables were assessed using Pearson's correlation coefficient. All statistical tests were two-tailed. A p value <0.05 was considered to indicate statistical significance. Analyses were performed using NCSS 8 (NCSS Statistical Software, Kaysville, Utah, USA). A supervised machine learning algorithm was used to identify a polynomial equation that best classified RD and Non-RD regions based on combined FD and FE values.

Figure 6:
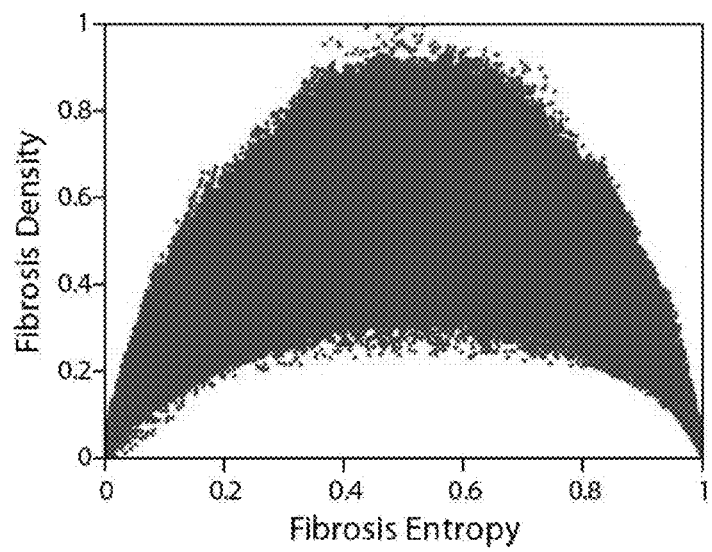
FIG. 6 shows the feature space of all fibrosis density (FD) and fibrosis entropy (FE) values in the atria in all Persistent Atrial Fibrillation (PsAF)-inducible models.
Figures 7A, 7B:
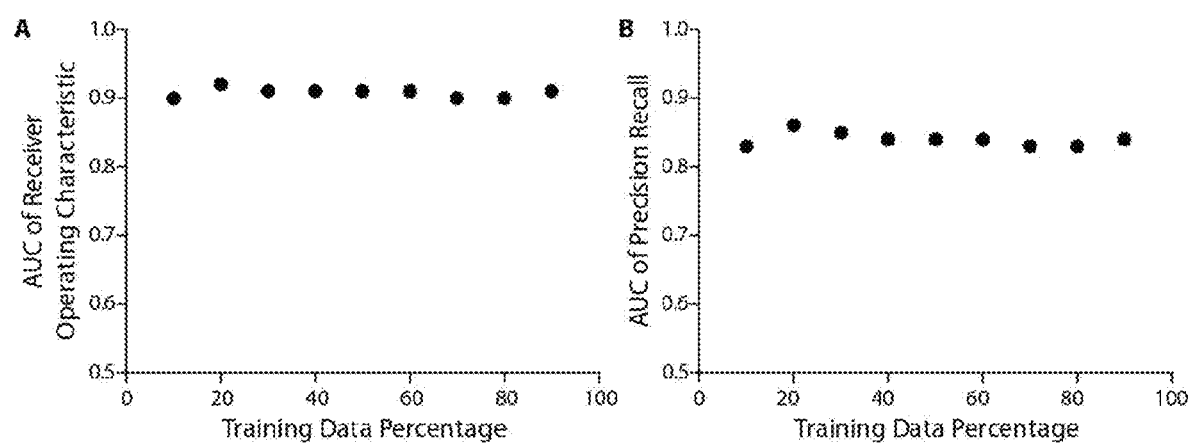
FIG. 7A shows a sensitivity analysis of the machine learning algorithm effectiveness when the algorithm was trained on different training sets (i.e., different percentages of all Reentrant Driver-Associated Phase Singularity (RD-PS) and non-RD-PS regions), wherein algorithm effectiveness was assessed by the area under the curve in receiver operating characteristic.
FIG. 7B shows a sensitivity analysis of the machine learning algorithm effectiveness when the algorithm was trained on different training sets (i.e., different percentages of all RD-PS and non-RD-PS regions), wherein algorithm effectiveness was assessed by the area under the curve in precision recall analyses.

In order to perform supervised machine learning, we used a support vector machine with a second-degree polynomial kernel to classify RD-PS and non-RD-PS regions based on FD and FE values. A second degree polynomial kernel was chosen because the feature space of all FD and FE values in all 13 PsAF-inducible atrial models resembled a concave down parabola (FIG. 6) and there were no distinct populations of FD and FE values that could be directly separated (i.e., with a line). We trained the machine-learning algorithm on 50% of all RD-PS and non-RD-PS regions and tested the algorithm's effectiveness on the remaining data. To assess the sensitivity of the machine learning algorithm, we changed the percentage of data on which we trained (ranging from 10% to 90% of all RD-PS and non-RD-PS regions) and reassessed the algorithm's effectiveness by analyzing the receiver operating characteristic and precision recall for each training set selection. Between different training sets, the algorithm's effectiveness was unchanged since the area under the curve for the receiver operator characteristic (FIG. 7A) and the precision recall analysis (FIG. 7B) remained 0.91 and 0.84, respectively.

Results

Patient Characteristics

The population studied comprised 20 patients (age 52±12 years, 3 women). All patients presented with PsAF, with a maximum uninterrupted duration of 9.3±6.7 months. Five (25%) patients had longstanding PsAF (duration >12 months). LA volume assessed via LGE-MRI was 73±22 mL/m2 (normalized to body surface area); biatrial and LA-only fibrosis burdens were 19.7±5.7% and 22.8±6.1%, respectively. LA fibrosis burden was categorized as Utah stage I in 0 (0%), stage II in 7 (35%), stage III in 9 (45%), and stage IV in 4 (20%) patients. The biatrial fibrosis burden was correlated to the uninterrupted AF duration (R=0.58, P<0.001) in each patient, but not to the LA volume (R=0.38, P=0.07) or age (R=0.34, P=0.10).

Patient-Specific Model Generation and in Silico AF Induction

The generation of personalized 3D atrial models was successful for all 20 patients; each model took ~20 hours to reconstruct, ~8 hours of which involved non-automated work. The average computing time required to simulate 1 second of activation was 47 min. The in silico stimulation protocol induced AF in 13 out of 20 patient-specific atrial models. Inducible models had significantly larger fibrosis burdens than non-inducible models (16.1±4.4 vs. 21.6±5.6, P=0.04). In the 13 inducible patient-specific models, the number of pacing sites from which AF could be induced was highly variable (mean 5/30 sites, ranging from 1 to 20) and related to biatrial fibrosis burden (R=0.62, P<0.001).

Characteristics of Simulated AF Episodes

Figure 8:
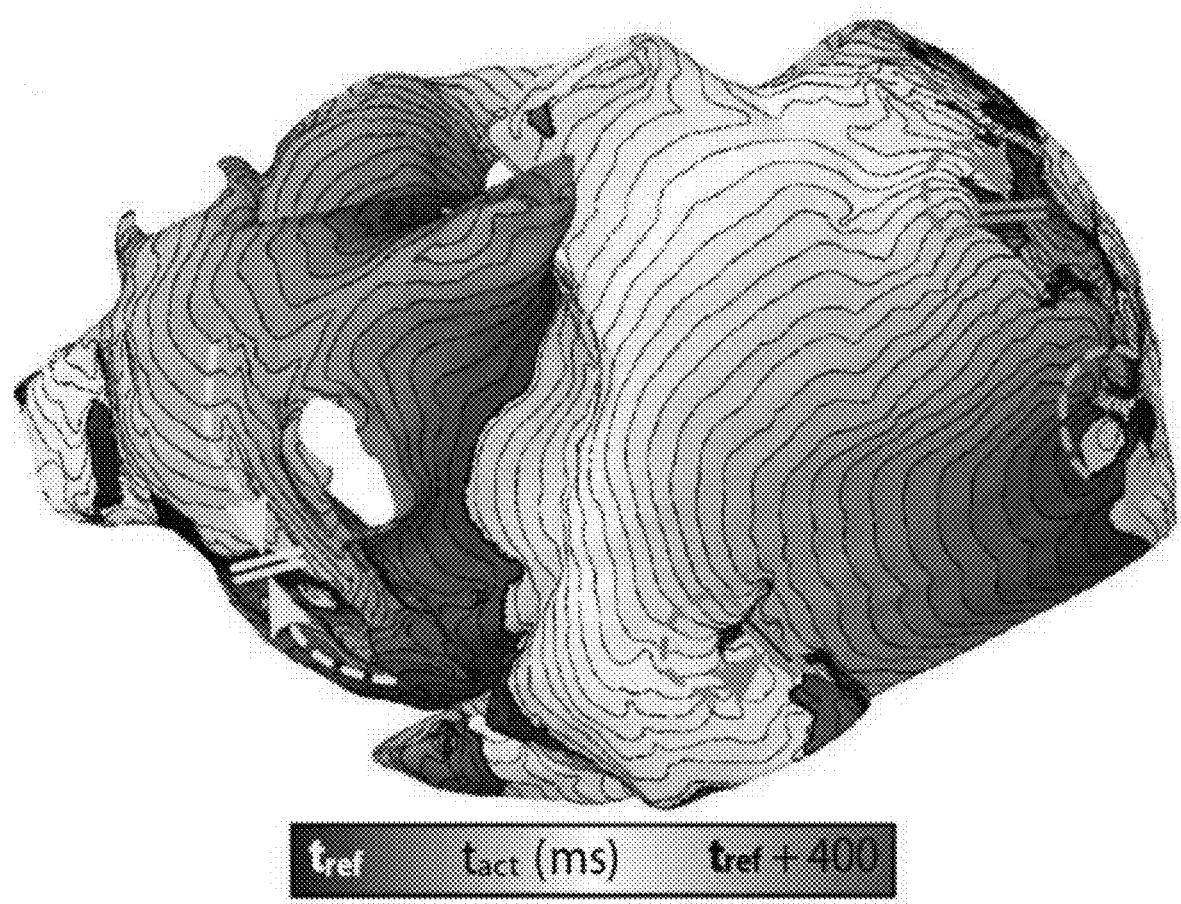
FIG. 8 shows an activation map of induced AF episode.
Figure 9:
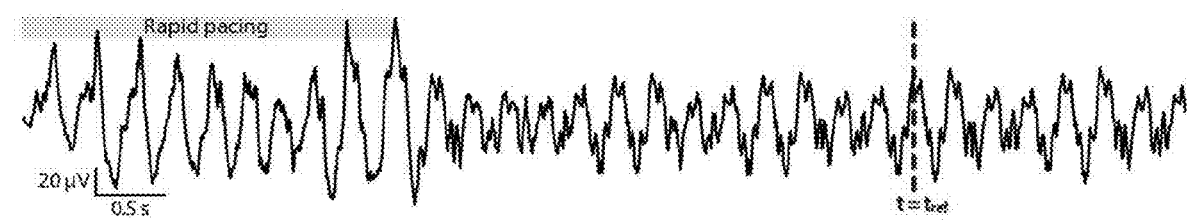
FIG. 9 shows a pseudo-electrogram recording of the arrhythmia reconstructed by differencing extracellular potential signals from points 4 cm away from the right and left atrial appendages.
Figures 10A, 10B, 10C, 10D:
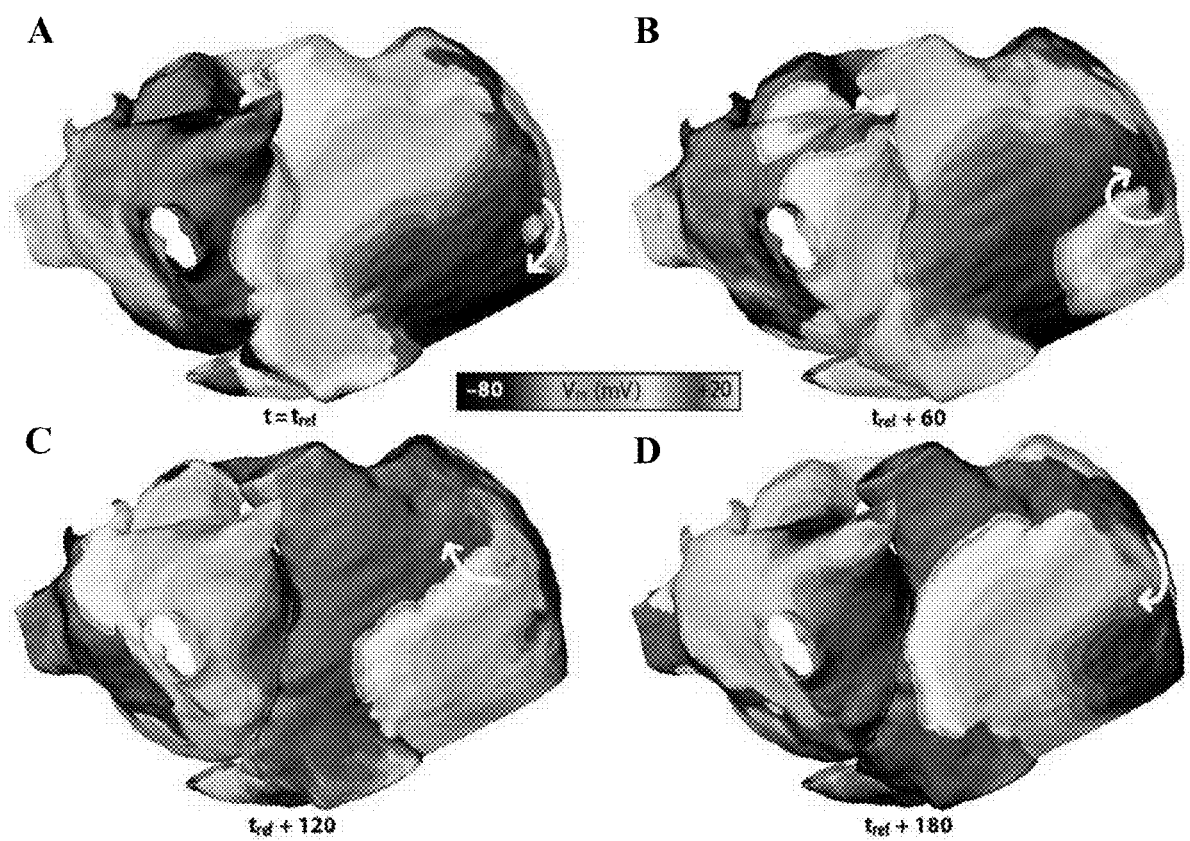
FIG. 10A shows a transmembrane potential ($V_m$) map at a first time instant during the AF episode.
FIG. 10B shows a transmembrane potential ($V_m$) map at a second time instant during the AF episode.
FIG. 10C shows a transmembrane potential ($V_m$) map at a third time instant during the AF episode.
FIG. 10D shows a transmembrane potential ($V_m$) map at a fourth time instant during the AF episode.
Figures 11A, 11B, 11C, 11D, 11E, 11F, 11G, 11H:
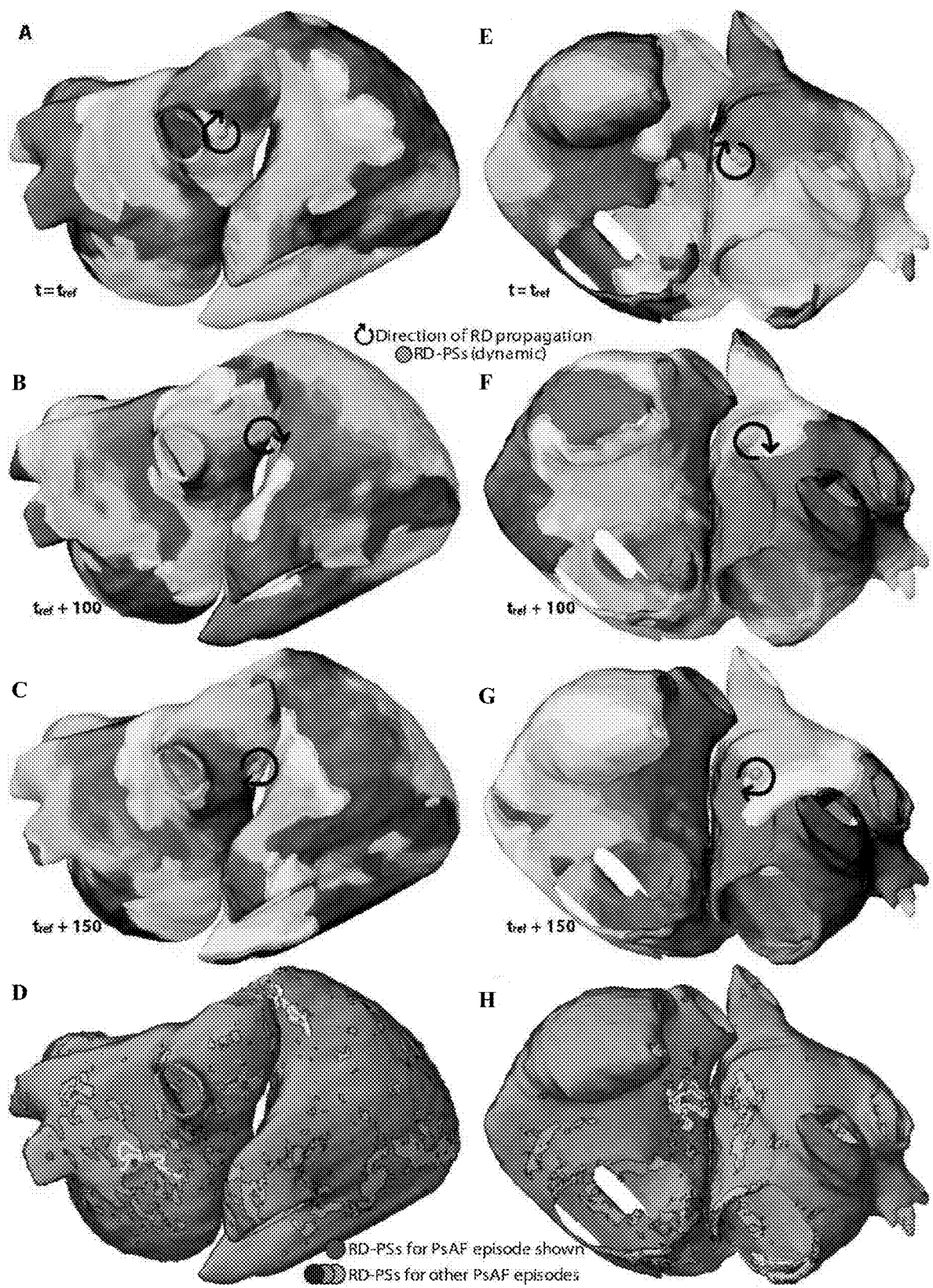
FIG. 11A shows a $V_m$ maps during AF for atrial model #1 at a first time instant.
FIG. 11B shows a $V_m$ maps during AF for atrial model #1 at a second time instant.
FIG. 11C shows a $V_m$ maps during AF for atrial model #1 at a third time instant.
FIG. 11D shows the aggregate locations of RD-PSs for all AF episodes observed in patient model #1, wherein distinct colors reflect RD-PSs observed for distinct AF morphologies.
FIG. 11E shows a $V_m$ map during AF for atrial model #16 at a first time instant.
FIG. 11F shows a $V_m$ map during AF for atrial model #16 at a second time instant.
FIG. 11G shows a $V_m$ map during AF for atrial model #16 at a third time instant.
FIG. 11H shows the aggregate locations of RD-PSs for all AF episodes in patient model #16.

In silico AF induction by programmed electrical stimulation and the subsequent activation patterns are illustrated in FIGS. 5, 8, 9, and 10A-10D. FIG. 5 illustrates locations of 30 sites where rapid pacing was applied for patient model #3. FIG. 8 shows an activation map of induced AF episode. The location of the RD is in the posterior right atrium (green arrow to the right). There were instances of transient reentries near the superior and inferior vena cava (red arrows in the middle) and conduction block in the posterior left atrium (yellow arrows to the left). FIG. 9 shows a pseudo-electrogram recording of the arrhythmia reconstructed by differencing extracellular potential signals from points 4 cm away from the right and left atrial appendages. FIGS. 10A-10D show a sequence of transmembrane potential ($V_m$) maps at four different time instants during the AF episode. The reference time (tref) of these $V_m$ maps are indicated by blue dashed arrows in FIG. 9. The RD in the posterior right atrium is indicated with white arrows.

In all 13 AF-inducible models, and for all AF morphologies, AF was driven by persistent RDs that formed in only a few atrial regions (FIG. 8, green arrow); there were 1 to 5 such RDs in each model (average 2.7±1.5). The activation pattern distal from each persistent RD was disorganized and fibrillatory, with multiple instances of transient reentry (FIG. 8, red arrows) and areas of conduction block (FIG. 8, yellow arrows). The complex activation pattern observed during simulated AF was associated with irregular pseudo-electrograms (FIG. 9). $V_m$ maps in FIGS. 10A-10D detail an episode of AF maintained by an RD in the posterior right atrium of patient model #3 (white arrows).

FIGS. 11A-11C and 11E-11G show $V_m$ maps during AF in models #1 and #16, respectively. The locations of RD-PSs and direction of RD propagation are indicated with purple circles and black arrows, respectively. The dynamic locations of RD-PSs over time for these AF episodes show that RDs persisted in spatially confined regions. For all unique AF morphologies observed in all models, the maximum RD-PS trajectory length was <10 mm (average: 7.57±2.33 mm). FIGS. 11D and 11H show RD-PS trajectories for all unique AF morphologies observed in models #1 and #16, respectively (red circles correspond to AF episodes shown in FIGS. 11A-11C and 11E-11G.

Local Fibrosis Characteristics at Reentrant Driver Sites

Figures 12A, 12B, 12C, 12D, 12E, 12F:
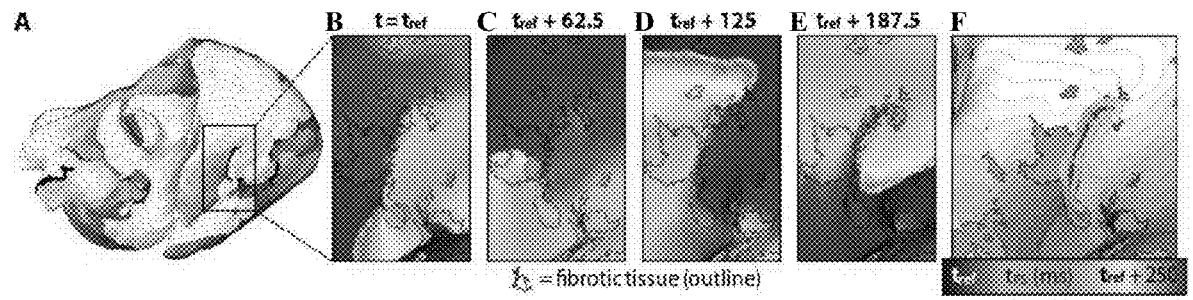
FIG. 12A shows the activation sequence of an AF episode maintained by an RD near the inferior vena cava in model #1.
FIG. 12B highlights a $V_m$ map of the same RD and its RD-PS locations at a first time instant, along with the outlines of fibrotic tissue.
FIG. 12C highlights a $V_m$ map of the same RD and its RD-PS locations at a second time instant, along with the outlines of fibrotic tissue.
FIG. 12D highlights a $V_m$ map of the same RD and its RD-PS locations at a third time instant, along with the outlines of fibrotic tissue.
FIG. 12E highlights a $V_m$ map of the same RD and its RD-PS locations at a fourth time instant, along with the outlines of fibrotic tissue.
FIG. 12F shows the trajectory of RD-PS movement over time superimposed on the activation map of the reentry and the fibrosis spatial pattern (green regions)

To better understand the dynamics of RDs induced in each atrial model, we analyzed the relationship between RD-PSs and the fibrosis spatial pattern. FIG. 12A shows the activation sequence of an AF episode maintained by an RD near the inferior vena cava in model #1, and FIGS. 12B-12E highlight $V_m$ maps of the same RD and its RD-PS locations at four different time instants, along with the outlines of fibrotic tissue. RD-PSs are marked with purple circles. The fibrotic tissue region boundaries are indicated by black outlines. At these time instants and throughout the reentry (FIG. 12F), the RD-PS dynamic location was along a trajectory that followed a boundary between fibrotic and non-fibrotic tissue (FIG. 12F). Trajectory of RD-PS movement over time superimposed on the activation map of the reentry and the fibrosis spatial pattern (green regions). Each discretely colored circle marks an RD-PS location at a unique instant of time.

Figures 13A, 13B, 13C, 13D, 13E, 13F, 13G, 13H:
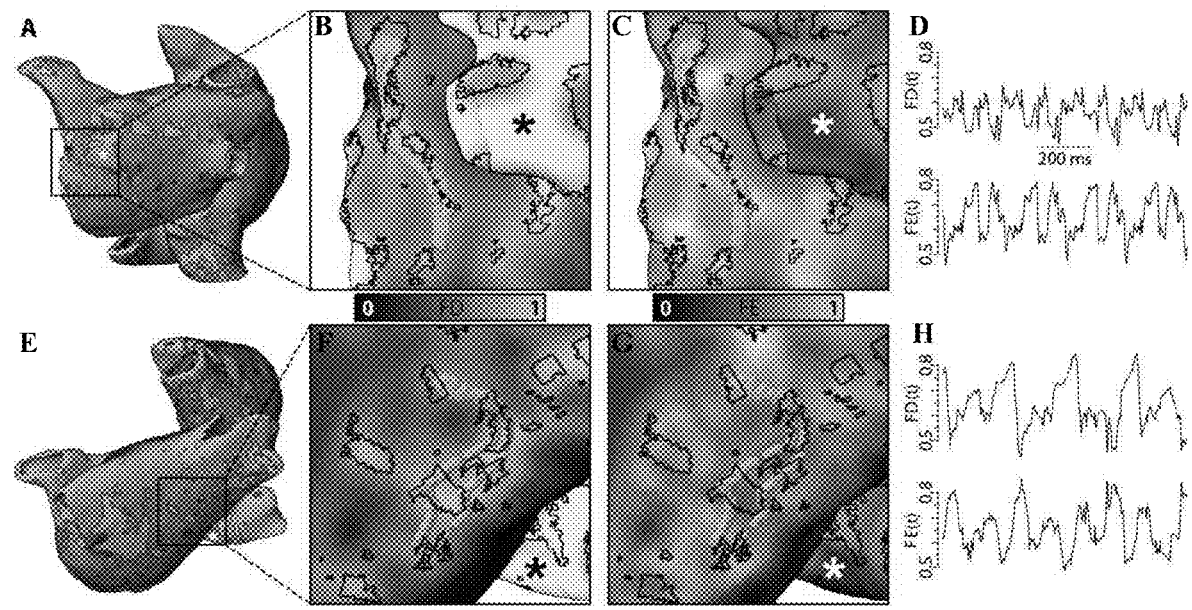
FIG. 13A shows the fibrotic tissue distribution near the left pulmonary veins for patient model #6, where an RD was observed.
FIG. 13B shows a map of FD in the area shown in FIG. 13A, wherein fibrotic tissue boundaries are outlined in black.
FIG. 13C shows a map of FE in the area shown in FIG. 13A, wherein fibrotic tissue boundaries are outlined in black.
FIG. 13D shows a time series plot of FD and FE at RD-PS locations for the case shown in FIG. 13A.
FIG. 13E shows the fibrotic tissue distribution in the posterior left atrium for patient model #8, where an RD was observed in a AF episode.
FIG. 13F shows a map of FD, fibrotic tissue boundaries, RD-PS locations, and regions of dense fibrotic tissue as described in FIG. 13E.
FIG. 13G shows a map of FE, fibrotic tissue boundaries, RD-PS locations, and regions of dense fibrotic tissue as described in FIG. 13E.
FIG. 13H shows a time series plot of FD and FE at RD-PS locations for the case shown in FIG. 13E.

Maps of the distributions of fibrosis metrics FD and FE in each atrial model were used to quantify the spatial characteristics of the regional fibrosis pattern where RDs persisted. FIGS. 13A-13C and 13E-13G show the distribution of fibrotic tissue in models #6 and #8. The inset panels present zoomed-in views of FD and FE maps. The locations of RD-PSs at each time instant are indicated with purple circles. RD-PSs were dynamically located in regions with high FD and FE values (orange areas). Black and white asterisks mark regions of dense fibrotic tissue with high FD, but low FE—RD-PSs were not observed in these areas. FIGS. 13D and 13H provide RD-PS trajectories and outlines of fibrotic regions. As the figures demonstrate, RD-PSs were located in atrial tissue with relatively high values of both FD and FE (>0.45, corresponding to orange colored regions). Regions with this characteristic corresponded to a subset of fibrotic tissue boundaries with extensive intermingling between fibrotic and non-fibrotic tissue. RD-PSs were not observed in regions of dense fibrotic tissue (e.g., sites marked by asterisks in FIGS. 13A-13C and 13E-13G). FIGS. 13D and 13H show time series plots of FD and FE values at RD-PS locations during one second of AF for the episodes shown in FIGS. 13A-13C and 13E-13G, respectively. FD and FE values range from 0.45 to 0.8.

Figures 14A, 14B, 14C, 14D:
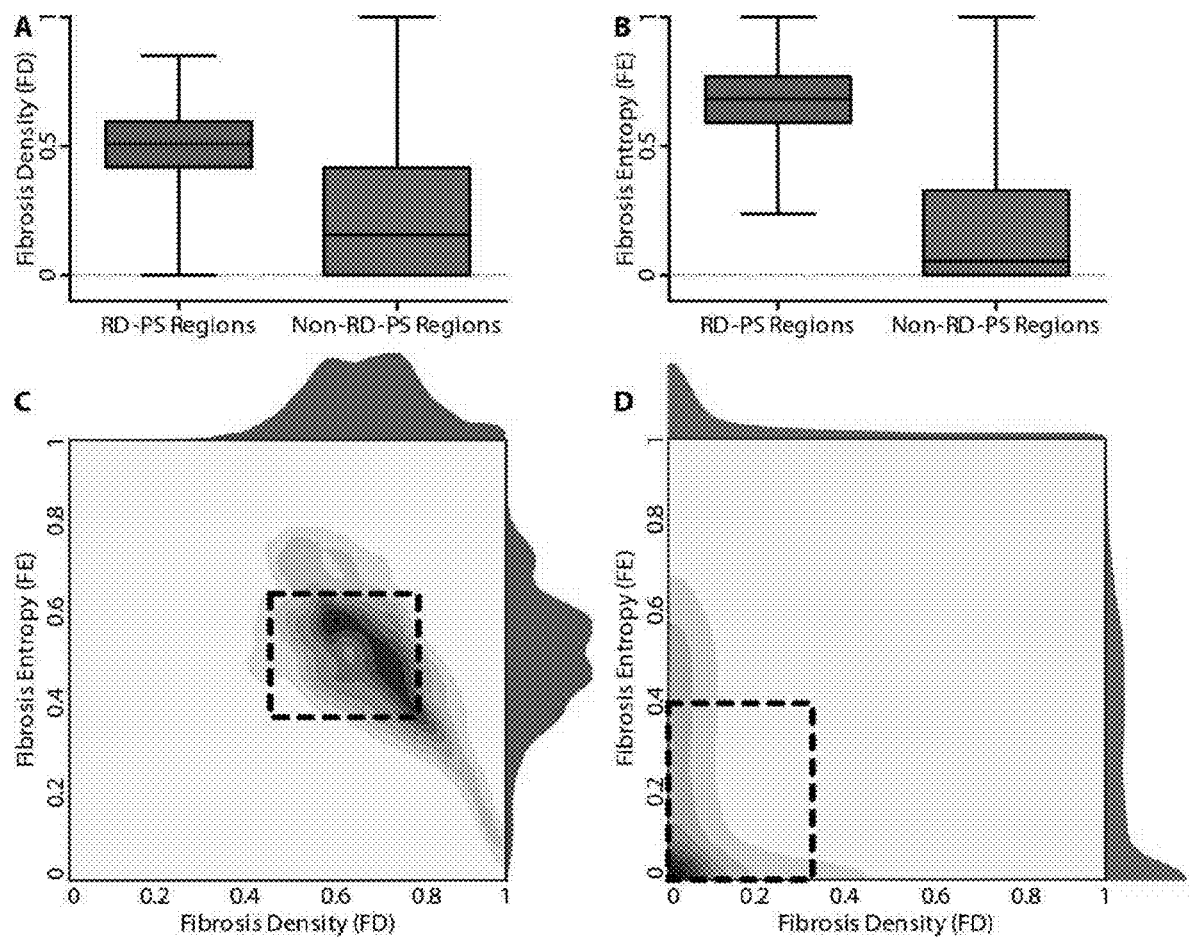
FIG. 14A shows a boxplot of FD at regions of atrial tissue where RD-PSs persisted (RD-PS regions) and where RD-PSs did not occur (non-RD-PS Regions) for all AF episodes in all atrial models.
FIG. 14B shows a boxplot of FE at RD-PS regions and non-RD-PS regions for all AF episodes in all atrial models.
FIG. 14C shows a 2D histogram of the FE and FD values at RD-PS regions for all AF episodes in all atrial models.
FIG. 14D shows a 2D histogram of FE and FD values at non-RD-PS regions for all AF episodes in all atrial models.

FIGS. 14A-14D show a summary of FD and FE characteristics at RD-PS locations for all AF episodes in all atrial models. FIG. 14A shows a boxplot of FE at regions of atrial tissue where RD-PSs persisted (RD-PS regions) and where RD-PSs did not occur (non-RD-PS Regions) for all AF episodes in all atrial models. FE in RD-PS regions is significantly higher than FE in non-RD-PS regions (IQR: 0.42-0.60 vs 0.00-0.40, p<0.05). FIG. 14B shows a boxplot of FD at RD-PS regions and non-RD-PS regions for all AF episodes in all atrial models. FD in RD-PS regions is significantly higher than FD in non-RD-PS regions (IQR: 0.59-0.769 vs 0.00-0.33, p<0.05). FIG. 14C shows a 2D histogram of the FE and FD values at RD-PS regions for all AF episodes in all atrial models. Right and top panels show the respective 1D histogram of just FE (right) and FD (top). Boxed region encloses FE and FD values ($0.37 \leq FE \leq 0.65$; $0.46 \leq FD \leq 0.80$) within one standard deviation of the mean of the FD and FE in RD-PS regions. FIG. 14D shows a 2D histogram of FE and FD values at non-RD-PS regions for all AF episodes in all atrial models. Right and top panels show the respective 1D histogram of just FE (right) and FD (top). Boxed region encloses FE and FD values ($0 \leq FE \leq 0.40$; $0 \leq FD \leq 0.32$) within one standard deviation of the mean of the FD and FE in non-RD-PS regions.

In the 13 AF-inducible atrial models, regions containing the RD-PS trajectories (i.e., RD-PS regions) had significantly higher FE (IQR: 0.42-0.60 vs 0.00-0.40, p<0.05) (FIG. 14A) and FD (IQR: 0.59-0.769 vs 0.00-0.33, p<0.05) (FIG. 14B) values compared to regions where RD-PSs did not occur (i.e., non-RD-PS regions). RD-PS regions had an FD of 0.63±0.17 and FE of 0.51±0.14 (FIG. 14C). Non-RD-PS regions had an FD of 0.13±0.19 and FE of 0.18±0.22 (FIG. 14D).

Figures 15A, 15B, 15C, 15D, 15E:
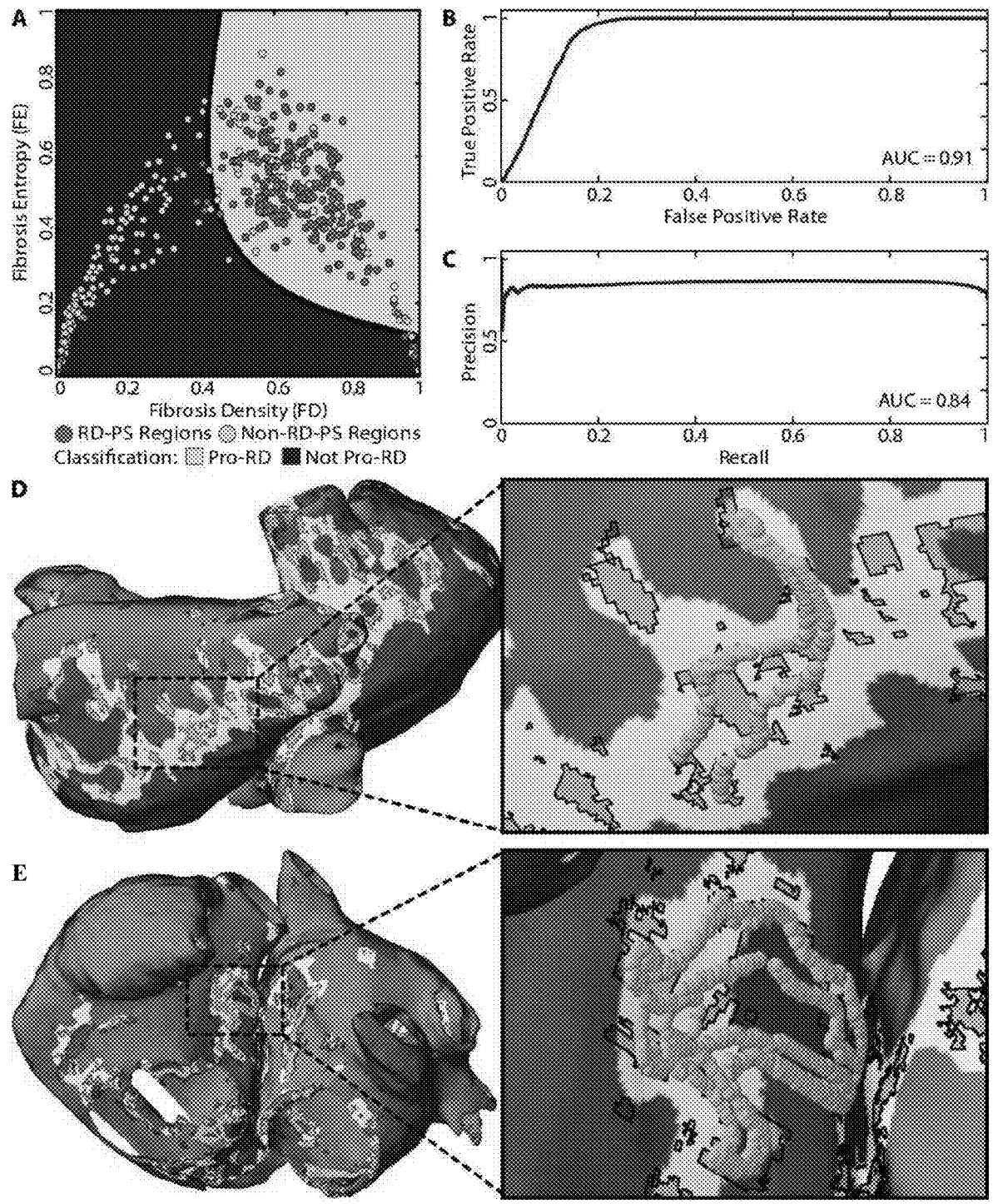
FIG. 15A illustrates classification of RD-PS and non-RD-PS regions.
FIG. 15B shows a receiver operating characteristic analysis of the machine learning algorithm.
FIG. 15C shows a precision-recall analysis of the machine learning algorithm.
FIG. 15D shows the location of RD-PSs in patient model #8 overlaid on the regions of the atria with the characteristic FD and FE values predicted to contain RD-PSs (green)
FIG. 15E shows the location of RD-PSs in patient model #16 overlaid on the regions of the atria with the characteristic FD and FE values predicted to contain RD-PSs (green)

A supervised machine-learning algorithm was used to identify a polynomial equation that best classified RD-PS and non-RD-PS regions based on FD and FE values. FIG. 15A illustrates classification of RD-PS and non-RD-PS regions. The polynomial equation that separated RD-PS (purple circles) and non-RD-PS regions (yellow circles) is indicated with a black line. The FD and FE values that characterized RD-PS regions and non-RD-PS regions are indicated in green (Pro-RD) and blue (Not Pro-RD), respectively. FIG. 15B shows a receiver operating characteristic analysis of the machine learning algorithm. The area under the curve (AUC) for this plot was 0.91. The receiver operating characteristic analysis demonstrated that the resulting classification had minimal false positive selection of RD-PS regions (AUC=0.91). FIG. 15C shows a precision-recall analysis of the machine learning algorithm. The area under the curve (AUC) for this plot was 0.84. The precision-recall analysis indicated that the approach had minimal false negative selection of non-RD-PS regions (AUC=0.84). Taken together, the latter two analyses demonstrated that our approach to identifying RD-PS regions was robust to over- and under-fitting. FIG. 15D shows the location of RD-PSs in patient models #8 (top) and #16 (bottom) overlaid on the regions of the atria with the characteristic FD and FE values predicted to contain RD-PSs (green). 13.79±4.93% of all atrial tissue had this characteristic fibrosis pattern; 83.50±2.35% of all RD-PSs were in these regions. Atrial tissue with the specific FD and FE characteristics identified by the machine-learning algorithm (i.e., regions with an FD/FE properties in the green region of FIG. 15A) corresponded to a subset of fibrotic region boundary zones (FIG. 15D). Although only 13.79±4.93% of all atrial tissue had this characteristic fibrosis spatial pattern, such tissue was present in 83.50±2.35% of all locations where RD-PSs occurred dynamically in the 13 AF-inducible patient-specific atrial models.

DISCUSSION

To the best of our knowledge, this is the largest computational modeling study ever undertaken on atrial electrophysiology. In 20 patient-specific atrial models with individualized fibrosis distributions derived from LGE-MRI, we showed that (i) AF is inducible by programmed electrical stimulation in models that have a sufficient amount of fibrosis, (ii) the induced AF is perpetuated by RDs that persist in spatially confined regions, and (iii) the latter regions constitute boundary zones between fibrotic and non-fibrotic tissue that are characterized with high fibrosis density and entropy values.

Generation of Patient-Specific Atrial Models and AF Induced in the Fibrotic Substrate The characteristics of the studied population were similar to those of the usual population presenting with PsAF in terms of age, gender, and PsAF duration, as well as atrial volume and fibrosis burden. [8, 9, 36] The method used to segment fibrosis from LGE-MRI data is based on prior reports, [7, 36, 37] and the relationship between fibrosis burden and PsAF duration is consistent with past studies. [8] In the atrial models constructed from the patient LGE-MRI scans, representation of atrial electrophysiology at the cell, tissue, and organ level in fibrotic and non-fibrotic regions were based on a large body of evidence from human, [22, 23, 38] animal, [25-27] and computational studies. [19-21] Arrhythmogenic properties of the fibrotic substrate were evaluated by programmed electrical stimulations using a dynamic pacing train delivered from a large number of locations throughout the atria. Using this protocol, AF was induced in 13/20 models, which contained a greater amount of fibrosis than the seven non-inducible models.

Since our modeling study was designed to evaluate the arrhythmogenic propensity of the fibrotic substrate, it did not include a representation of intrinsic focal drivers. In patients, PsAF is perpetuated by a complex interplay between RDs and focal drivers. [4-6, 39] This offers a potential explanation for why we could not induce arrhythmia in seven atrial models: in these patients, triggered activity may have been the predominant mechanism that perpetuated PsAF. Another potential explanation for non-inducibility in these models could be the inaccurate quantification of fibrosis from LGE-MRI in the corresponding patients and the omission of diffuse fibrosis, which is inaccessible from current imaging methods. [7]

Characteristics of Simulated AF Episodes Induced by Programmed Electrical Stimulation The analysis of AF dynamics in inducible atrial models showed a combination of sustained RDs, transient reentries, wave collisions, and functional blocks all of which have been described in mapping studies of PsAF in humans. [40] These complex activation patterns were associated with irregular pseudo-electrograms, which were qualitatively similar to clinical electrograms of PsAF. [41] Our results confirm that PsAF can be perpetuated by RDs that dynamically emerge in a limited number of locations (1 to 5 unique RD domains per patient; average: $2.69 \pm 1.54$). In simulations, RDs persisted for the duration of the entire simulation period (2.5 s). Phase singularities associated with each RD were not stationary but meandered within spatially restricted regions (average extent: $7.57 \pm 2.33$ mm). These findings are consistent with observations of RD dynamics in PsAF from recent clinical studies in terms of the number, size, and stability of RD domains. Haïssaguerre et al. [5] used inverse electrocardiography (ECGI) in pre-ablation PsAF patients and identified between 2 and 6 distinct RD domains in each individual. Furthermore, regions where RDs were observed most frequently were found to be of limited extent, and therefore amenable to catheter ablation. [5, 36] Likewise, FIRM-guided ablation studies [6] in PsAF patients reported a small number of drivers (total of $2.2 \pm 1.0$ per patient, although reentrant and focal sources were not separately reported), with RDs that meandered within compact regions (1-2 cm$^2$).

As mentioned above, the present study did not include automatic focal activity. We anticipate that the addition of paroxysmal triggered activations would not affect our primary finding that RDs occur at a subset of fibrosis boundary zones, but may affect the stability of observed RDs, shortening their lifespan. For example, we expect that a focal driver might dislodge an RD from one fibrotic region, leading it to meander through the atria and/or re-anchor to a different location with the same characteristics of the fibrosis pattern. Such dynamics of PsAF would be consistent with findings from ECGI, [5] where RDs occur most frequently in spatially restricted regions but also move between such regions, with shorter lifespans at each anchoring site (typically <1 s).

Characteristics of the Fibrosis Pattern in Regions where RDs Persist

Fibrosis architecture is highly variable from patient to patient in the PsAF population, as well as from region to region within the atria of a given patient. [8, 9] In our simulations of AF in the fibrotic substrates, RDs are only observed in a limited number of atrial sites. Therefore, we hypothesized that the fibrosis spatial pattern necessary to anchor reentry was highly specific. For all induced AF episodes in all atrial models, the confined regions within which the RD-PSs meandered had a consistent fibrosis spatial pattern, characterized by high values of both FD and FE ($0.37 \leq FE \leq 0.65$; $0.46 \leq FD \leq 0.80$). This combination of metrics corresponds to atrial locations with a high degree of intermingling between fibrotic and non-fibrotic tissue. RD-PSs were conspicuously absent from both completely non-fibrotic sites and regions of deep fibrosis (i.e., locations with high FD and low FE, such as those marked by asterisks in FIGS. 13A-13C and 13E-13G). This is a key observation because it expands upon the recent clinical finding that RDs identified by ECGI are co-localised with fibrosis boundary zones identified by LGE-MRI. [37] Our results demonstrate that only a limited subset of fibrosis border zones has the characteristics (i.e., high FD and high FE) needed to sustain RDs. The use of sophisticated machine learning tools enabled us to devise a sensitive and specific classification scheme capable of pinpointing the combination of FD and FE metric values associated with RD localization.

Regions with both high FD and high FE are a potent substrate for the initiation and perpetuation of RDs because such locations are associated with steep spatial gradients in excitability and refractoriness, rendering them highly prone to conduction failure [10] due to the extensive intermingling of fibrotic and non-fibrotic tissue. As part of the border zones of fibrotic remodeling, these RD regions are in contact with both non-fibrotic tissue, which allows propagating wavefronts to rapidly pivot around zones of functional block, [42] and with deeper fibrotic regions that ensure sufficient conduction slowing [11-13] to sustain reentry. The average size of the RD-perpetuation regions in our study ($7.57 \pm 2.33$ mm) is consistent with findings from previous simulation and experimental work demonstrating that RDs are attracted to and/or anchored by inhomogeneties of a similar spatial scale (4.5 to 10 mm) resulting from gradients in ion channel expression [43, 44] or APD. [45]

Clinical Perspectives

Knowledge regarding the link between dynamic RD localization and the spatial characteristics of the fibrotic substrate, as acquired in this study, has important implications for clinical strategies to manage and treat PsAF in patients. Multiple centres have reported that ablation of RD-harboring sites can terminate PsAF or convert it to a more clinically manageable tachycardia, [5, 6] but it remains unclear why this type of targeting has therapeutic value. Our results suggest that this success may be attributable to the fact that such ablations "homogenize" the tissue in a RD-anchoring region, rendering it more like a deeper fibrotic region with less interdigitation of fibrotic and non-fibrotic tissue. It is also conceivable that locations with FD/FE favoring RD localization, as identified by processing the LGE-MRI images, could be directly targeted for ablation, consistent with current clinical concepts of substrate modification [46] for PsAF ablation. Of note, the total amount of atrial tissue with such high FD/FE combination in each patient was relatively small (13.8±4.9% of the atria). RDs in our study were found to persist in not all, but a portion of the regions with high FD/FE (see FIGS. 15D and 15E). It is likely that other pacing sites, in addition to the 30 used in each patient-specific model, will result in the formation of persistent RDs in the reminder of high FD/FE tissue. We further speculate that following ablation of a region sustaining an RD, new emergent RDs will localize to sites with the same (high FD/FE) fibrosis spatial characteristics. As such, the percentage cited above should be interpreted as the theoretical maximum amount of tissue that must be ablated to eliminate the RD-perpetuating properties of the fibrotic substrate. Future work will be needed to determine whether and how this tissue subset could be further narrowed towards achieving truly optimal ablation lesion sets.

Study Factors

One factor of this study is related to the reconstruction of personalized models from LGE-MRI data. The ability to derive realistic representations of atrial fibrosis from LGE-MRI is highly dependent on scan quality and operator experience. [7] Although the studied patient-specific models had a wide range of global fibrosis burdens (ranging from 10.8 to 33.4% of the biatrial wall) and a diversity of fibrosis spatial patterns, the localization of RDs at sites with high FD and FE was remarkably consistent from model to model. This suggests that the central finding of our study is relatively insensitive to the inherent factors of LGE-MRI—if models were reconstructed using a different segmentation threshold, the absolute locations of RDs would undoubtedly change but the underlying fibrosis spatial pattern would be the same.

Another factor is the absence of correlation with clinical characteristics, particularly mapping and outcome data, which were unavailable. This prevented us from assessing the predictive value of simulation results with respect to clinical outcomes. Indeed, the in silico inducibility and the number of RD sites might be interesting MRI-derived prognostic markers as they include not only the fibrosis burden, but also the impact of fibrosis architecture on PsAF mechanisms. Finally, the recognition of specific structural features derived from LGE-MRI (sites with high FE and FD) might also be a prognostic marker for PsAF outcomes.

CONCLUSION

We demonstrated that reconstruction of personalized 3D atrial models with individualized fibrosis patterns from LGE-MRI is feasible. Dynamic pacing from a number of locations was able to induce AF in atrial models that included sufficient amounts of fibrosis. Simulations demonstrated that AF in the fibrotic substrate is perpetuated by RDs localized in boundary zones between fibrotic and non-fibrotic tissue that are characterized with high fibrosis density and entropy. These results provide new insights into the mechanisms of PsAF perpetuation and pave the way towards an MRI-based approach for the personalization of clinical management in patients with PsAF.

References—Example 1

[1] Andrade J, Khairy P, Dobrev D, Nattel S. The clinical profile and pathophysiology of atrial fibrillation: relationships among clinical features, epidemiology, and mechanisms. Circ Res 2014; 114: 1453-1468.

[2] Verma A, Jiang C Y, Betts T R, Chen J, Deisenhofer I, Mantovan R, et al. Approaches to catheter ablation for persistent atrial fibrillation. N Engl J Med 2015; 372: 1812-1822.

[3] Nattel S, Guasch E, Savelieva I, Cosio F G, Valverde I, Halperin J L, et al. Early management of atrial fibrillation to prevent cardiovascular complications. Eur Heart J 2014; 35: 1448-1456.

[4] Mandapati R, Skanes A, Chen J, Berenfeld O, Jalife J. Stable microreentrant sources as a mechanism of atrial fibrillation in the isolated sheep heart. Circulation 2000; 101: 194-199.

[5] Haissaguerre M, Hocini M, Denis A, Shah A J, Komatsu Y, Yamashita S, et al. Driver domains in persistent atrial fibrillation. Circulation 2014; 130: 530-538.

[6] Narayan S M, Krummen D E, Shivkumar K, Clopton P, Rappel W J, Miller J M. Treatment of atrial fibrillation by the ablation of localized sources: CONFIRM (Conventional Ablation for Atrial Fibrillation With or Without Focal Impulse and Rotor Modulation) trial. J Am Coll Cardiol 2012; 60: 628-636.

[7] Oakes R S, Badger T J, Kholmovski E G, Akoum N, Burgon N S, Fish E N, et al. Detection and quantification of left atrial structural remodeling with delayed-enhancement magnetic resonance imaging in patients with atrial fibrillation. Circulation 2009; 119: 1758-1767.

[8] Marrouche N F, Wilber D, Hindricks G, Jais P, Akoum N, Marchlinski F, et al. Association of atrial tissue fibrosis identified by delayed enhancement MRI and atrial fibrillation catheter ablation: the DECAAF study. JAMA 2014; 311: 498-506.

[9] Cochet H, Mouries A, Nivet H, Sacher F, Derval N, Denis A, et al. Age, atrial fibrillation, and structural heart disease are the main determinants of left atrial fibrosis detected by delayed-enhanced magnetic resonance imaging in a general cardiology population. J Cardiovasc Electrophysiol 2015; 26: 484-492.

[10] Spach M S, Dolber P C, Heidlage J F. Interaction of inhomogeneities of repolarization with anisotropic propagation in dog atria. A mechanism for both preventing and initiating reentry. Circ Res 1989; 65: 1612-1631.

[11] Tanaka K, Zlochiver S, Vikstrom K L, Yamazaki M, Moreno J, Klos M, et al. Spatial distribution of fibrosis governs fibrillation wave dynamics in the posterior left atrium during heart failure. Circ Res 2007; 101: 839-847.

[12] Li D, Fareh S, Leung T K, Nattel S. Promotion of atrial fibrillation by heart failure in dogs: atrial remodeling of a different sort. Circulation 1999; 100: 87-95.

[13] Burstein B, Comtois P, Michael G, Nishida K, Villeneuve L, Yeh Y H, et al. Changes in connexin expression and the atrial fibrillation substrate in congestive heart failure. Circ Res 2009; 105: 1213-1222.

[14] Verheule S, Sato T, Everett Tt, Engle S K, Otten D, Rubart-von der Lohe M, et al. Increased vulnerability to atrial fibrillation in transgenic mice with selective atrial fibrosis caused by overexpression of TGF-beta1. Circ Res 2004; 94: 1458-1465.

[15] Hansen B J, Zhao J, Csepe T A, Moore B T, Li N, Jayne L A, et al. Atrial fibrillation driven by micro-anatomic intramural re-entry revealed by simultaneous sub-epicardial and sub-endocardial optical mapping in explanted human hearts. Eur Heart J 2015; 36: 2390-2401.

[16] Raya S P, Udupa J K. Shape-based interpolation of multidimensional objects. IEEE Trans Med Imaging 1990; 9: 32-42.

[17] Prassl A J, Kickinger F, Ahammer H, Grau V, Schneider J E, Hofer E, et al. Automatically generated, anatomically accurate meshes for cardiac electrophysiology problems. IEEE Trans Biomed Eng 2009; 56: 1318-1330.

[18] Krueger M, Schmidt V, Tobón C, Weber F, Lorenz C, Keller D J, et al. Modeling Atrial Fiber Orientation in Patient-Specific Geometries: A Semi-automatic Rule-Based Approach. In: Metaxas D and Axel L, eds. Functional Imaging and Modeling of the Heart. Springer Berlin Heidelberg 2011: 223-232.

[19] McDowell K S, Vadakkumpadan F, Blake R, Blauer J, Plank G, MacLeod R S, et al. Methodology for patient-specific modeling of atrial fibrosis as a substrate for atrial fibrillation. J Electrocardiol 2012; 45: 640-645.

[20] McDowell K S, Vadakkumpadan F, Blake R, Blauer J, Plank G, Macleod R S, et al. Mechanistic inquiry into the role of tissue remodeling in fibrotic lesions in human atrial fibrillation. Biophys J 2013; 104: 2764-2773.

[21] McDowell K S, Zahid S, Vadakkumpadan F, Blauer J, MacLeod R S, Trayanova N A. Virtual electrophysiological study of atrial fibrillation in fibrotic remodeling. PLoS One 2015; 10: e0117110.

[22] Courtemanche M, Ramirez R J, Nattel S. Ionic mechanisms underlying human atrial action potential properties: insights from a mathematical model. Am J Physiol 1998; 275: H301-321.

[23] Krummen D E, Bayer J D, Ho J, Ho G, Smetak M R, Clopton P, et al. Mechanisms of human atrial fibrillation initiation: clinical and computational studies of repolarization restitution and activation latency. Circ Arrhythm Electrophysiol 2012; 5: 1149-1159.

[24] Konings K T, Kirchhof C J, Smeets J R, Wellens H J, Penn O C, Allessie M A. High-density mapping of electrically induced atrial fibrillation in humans. Circulation 1994; 89: 1665-1680.

[25] Nattel S, Burstein B, Dobrev D. Atrial remodeling and atrial fibrillation: mechanisms and implications. Circ Arrhythm Electrophysiol 2008; 1: 62-73.

[26] Corradi D, Callegari S, Maestri R, Benussi S, Alfieri O. Structural remodeling in atrial fibrillation. Nat Clin Pract Cardiovasc Med 2008; 5: 782-796.

[27] Kakkar R, Lee R T. Intramyocardial fibroblast myocyte communication. Circ Res 2010; 106: 47-57.

[28] Avila G, Medina I M, Jimenez E, Elizondo G, Aguilar C I. Transforming growth factor-beta1 decreases cardiac muscle L-type Ca2+ current and charge movement by acting on the Cav1.2 mRNA. Am J Physiol Heart Circ Physiol 2007; 292: H622-631.

[29] Ramos-Mondragon R, Vega A V, Avila G. Long-term modulation of Na+ and K+ channels by TGF-beta1 in neonatal rat cardiac myocytes. Pflugers Arch 2011; 461: 235-247.

[30] Pedrotty D M, Klinger R Y, Kirkton R D, Bursac N. Cardiac fibroblast paracrine factors alter impulse conduction and ion channel expression of neonatal rat cardiomyocytes. Cardiovasc Res 2009; 83: 688-697.

[31] Vigmond E J, Aguel F, Trayanova N A. Computational techniques for solving the bidomain equations in three dimensions. IEEE Trans Biomed Eng 2002; 49: 1260-1269.

[32] Vigmond E J, Hughes M, Plank G, Leon L J. Computational tools for modeling electrical activity in cardiac tissue. J Electrocardiol 2003; 36 Suppl: 69-74.

[33] Narayan S M, Krummen D E, Rappel W J. Clinical mapping approach to diagnose electrical rotors and focal impulse sources for human atrial fibrillation. J Cardiovasc Electrophysiol 2012; 23: 447-454.

[34] Eason J, Trayanova N. Phase singularities and termination of spiral wave reentry. J Cardiovasc Electrophysiol 2002; 13: 672-679.

[35] Kriegel H-P, Kröger P, Sander J, Zimek A. Density-based clustering. WIREs Data Mining Knowl Discov 2011; 1: 231-240.

[36] Cochet H, Dubois R, Relan J, Zahid S, Aljefairi N, Yamashita S, et al. Relationship between rotor activity and fibrosis in persistent atrial fibrillation: a combined noninvasive mapping and MRI study Heart Rhythm. 2015: 5512.

[37] Jadidi A S, Cochet H, Shah A J, Kim S J, Duncan E, Miyazaki S, et al. Inverse relationship between fractionated electrograms and atrial fibrosis in persistent atrial fibrillation: combined magnetic resonance imaging and high-density mapping. J Am Coll Cardiol 2013; 62: 802-812.

[38] Courtemanche M, Ramirez R J, Nattel S. Ionic targets for drug therapy and atrial fibrillation-induced electrical remodeling: insights from a mathematical model. Cardiovasc Res 1999; 42: 477-489.

[39] Haissaguerre M, Jais P, Shah D C, Takahashi A, Hocini M, Quiniou G, et al. Spontaneous initiation of atrial fibrillation by ectopic beats originating in the pulmonary veins. N Engl J Med 1998; 339: 659-666.

[40] de Groot N M, Houben R P, Smeets J L, Boersma E, Schotten U, Schalij M J, et al. Electropathological substrate of longstanding persistent atrial fibrillation in patients with structural heart disease: epicardial breakthrough. Circulation 2010; 122: 1674-1682.

[41] Bollmann A, Sonne K, Esperer H D, Toepffer I, Langberg J J, Klein H U. Non-invasive assessment of fibrillatory activity in patients with paroxysmal and persistent atrial fibrillation using the Holter ECG. Cardiovasc Res 1999; 44: 60-66.

[42] Pandit S V, Jalife J. Rotors and the dynamics of cardiac fibrillation. Circ Res 2013; 112: 849-862.

[43] Shajahan T K, Sinha S, Pandit R. Spiral-wave dynamics depend sensitively on inhomogeneities in mathematical models of ventricular tissue. Phys Rev E Stat Nonlin Soft Matter Phys 2007; 75: 011929.

[44] Climent A M, Guillem M S, Fuentes L, Lee P, Bollensdorff C, Fernandez-Santos M E, et al. The Role of Atrial Tissue Remodeling on Rotor Dynamics: An In-Vitro Study. Am J Physiol Heart Circ Physiol 2015: ajpheart 00055 02015.

[45] Defauw A, Dawyndt P, Panfilov A V. Initiation and dynamics of a spiral wave around an ionic heterogeneity in a model for human cardiac tissue. Phys Rev E Stat Nonlin Soft Matter Phys 2013; 88: 062703.

[46] Hocini M, Sanders P, Jais P, Hsu L F, Takahashi Y, Rotter M, et al. Techniques for curative treatment of atrial fibrillation. J Cardiovasc Electrophysiol 2004; 15: 1467-1471.

Example 2: Prediction of Targets for Catheter Ablation of Persistent Atrial Fibrillation Based on Analysis of Patient-Specific Fibrosis Patterns AF is widely recognized as an emerging global health crisis. At present, 1-2% of individuals worldwide suffer from AF [1] and its prevalence is expected to increase 2.5-fold over the next 40 years due to the aging population. [2] Patients affected by AF have a higher mortality rate, largely due to a dramatically increased risk of thromboembolic stroke. [1] AF is also associated with severely impaired quality of life, [3] increased rates of cognitive impairment, [4] and high treatment costs. [5]

In a subset of patients, AF symptoms can be safely, reliably, and permanently eliminated by using catheter ablation to achieve electrical isolation of arrhythmia triggers in the pulmonary veins (PVs), a procedure called PV isolation. [6] However, outcomes of ablation procedures are low in patients with the long-standing or persistent form of the disease (PsAF), [7] which is defined by AF episodes that last ≥7 days. [8] This is an issue of considerable concern because the rate of progression in AF is rapid, with approximately 5% of patients transitioning to PsAF each year from the more clinically manageable paroxysmal form of AF. [9] The primary impediment to effective treatment of PsAF is that such patients experience significant atrial structural remodeling, [10, 11] giving rise to an extensive fibrotic substrate for arrhythmia perpetuation that cannot be eliminated by PV isolation. [6] Efforts to improve the efficacy of the clinical procedure in PsAF patients have been stymied by the fact that there is no concrete understanding of which sites should be ablated to eliminate the fibrotic substrate's arrhythmia-sustaining properties. [6] Clearly, there is an urgent need for new approaches for determining the optimal ablation targets in PsAF patients with atrial fibrosis.

The Fibrotic Substrate for Arrhythmia Perpetuation in PsAF Patients

Progression of AF to the persistent stage (PsAF) is associated with extensive structural remodeling, including increased atrial fibrosis. [12] The fibrogenesis signaling pathway is initiated by multiple AF-associated factors, including oxidative stress, mechanical stretch, and rapid atrial activation. [10, 13] Once activated, this cascade causes fibroblasts to proliferate and differentiate into myofibroblasts (i.e., activated fibroblasts), [11, 14] which synthesize excessive amounts of collagenous extracellular matrix [15, 16] and release paracrine signaling factors, including transforming growth factor (TGF)-β1. [17-19] Additionally, structural remodeling alters gap junction function via down-regulation, lateralization, and hypo-phosphorylation of connexin proteins. [20,21]

Collagen deposition and gap junction remodeling have significant effects on organ-scale electrophysiological behavior, leading to slowed conduction (disproportionately so in the direction transverse to cardiac fibers) and abnormal excitation characteristics in fibrotic regions. [21-23] Moreover, increased TGF-β1 leads to dramatic reduction of the fast sodium, L-type calcium, and inward rectifier potassium currents ($I_{Na}$, $I_{CaL}$, and $I_{K1}$), [24, 25] leading to increased action potential duration (APD), depolarized resting transmembrane potential, and decreased upstroke velocity in fibrotic myocardium. [24] All of the above electrophysiological changes provide mechanisms for unidirectional conduction block and slow propagation, [26] increasing the likelihood of reentrant source formation. [27-29] It is also known that spatial patterns of atrial fibrosis are complex and vary widely from individual to individual, which increases the variability and complexity of local activation patterns and global dynamics of arrhythmia. [27]

Based on the evidence reviewed above, it is clear that atrial fibrosis creates a substrate for perpetuation of PsAF. However, there is a lack of mechanistic understanding regarding how the specific distribution of fibrosis affects AF dynamics. Patient-specific atrial models are used herein to thoroughly explore the role of individual fibrotic distributions in AF dynamics. We also demonstrate that the dynamic locations of the persistent organizing centers of reentry in each patient are determined by the individual distribution of atrial fibrosis.

Catheter Ablation to Modify the Fibrotic Substrate

The success rate for PV isolation in patients with extensive atrial fibrosis, such as those with PsAF, is very low (≈30%). [30-33] Because of this, efforts have been made to extend ablation protocols to modify the fibrotic substrate so that its propensity to perpetuate arrhythmia is eliminated. One widely used strategy is to augment PV isolation by adding linear ablations between anatomical landmarks, such as the mitral isthmus and specific pulmonary veins, to mitigate regions of conduction slowing and block due to structural remodeling. [34-37] A second technique, still in the initial stages of clinical use, is focal impulse and rotor mapping (FIRM) ablation, [38-40] in which intra-cardiac electro-anatomic mapping is used to locate sites where signal patterns are indicative of local reentrant sources or triggered activity during PsAF; the sites are then ablated. In addition, attempts have been made to execute ablations at the locations of complex fractionated atrial electrograms (CFAEs); [41-43] however, recent studies have shown that mechanisms unrelated to arrhythmia give rise to electrogram fractionation [6] and that CFAE sites are usually remote from organizing centers of PsAF. [39] Although some of the techniques discussed above lead to better ablation outcomes than PV isolation alone in PsAF patients, success rates reported by clinical trials remain low (<75%) [38-43] and inter-center reproducibility is poor. [44] There are two reasons for this low efficacy: (1) a lack of understanding of exactly how structural remodeling influences PsAF dynamics, and (2) the fact that low-resolution point-wise mapping cannot fully capture the complexity of arrhythmia dynamics caused by the unique fibrosis distribution in each patient. [1, 6] Importantly, all approaches involve identification of ablation sites by catheter-based mapping of patient atria, which is invasive, tedious, and time-consuming. [45] This leads to a high rate of complications and extended procedure durations. [44]

From the brief review above, it is clear that ablation procedures designed to modify the fibrotic substrate remain ineffective in achieving freedom from AF in PsAF patients. They also universally require the use of invasive electro-anatomic mapping procedures for the identification of ablation sites. We describe herein a novel approach to non-invasively predict the optimal ablation targets for PsAF using simulations with personalized atrial models that incorporate patient-specific atrial geometry and fibrosis patterns obtained from pre-procedure LGE-MRI scans. A retrospective human study is used to validate this new strategy, paving the way towards a safer, more accurate approach to custom tailor PsAF ablation procedures.

Results

Figures 16A, 16B:
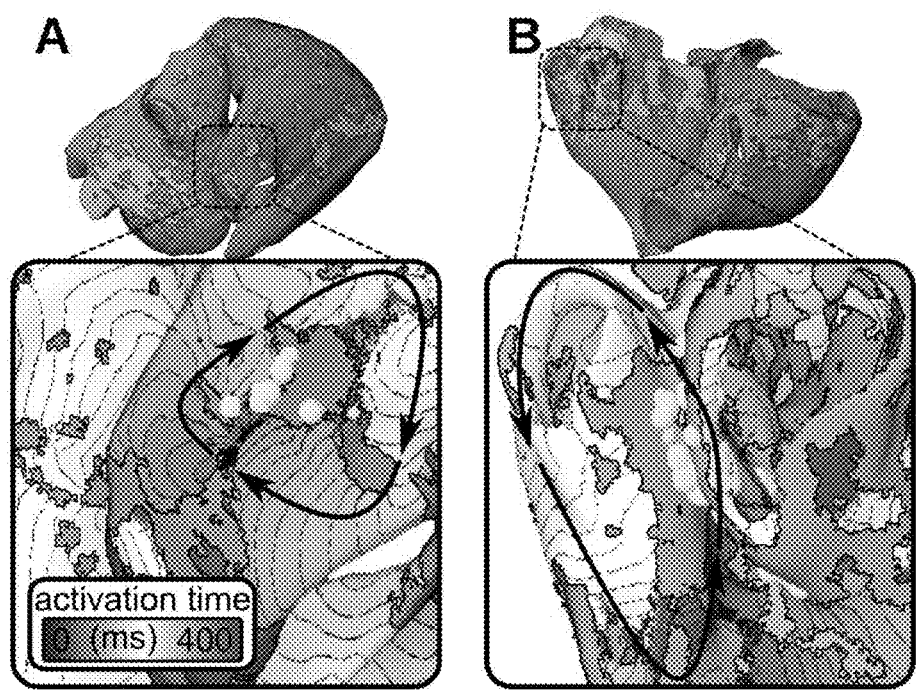
FIG. 16A shows a first patient-specific atrial model reconstructed from in vivo LGE-MRI data from a patient with PsAF.
FIG. 16B shows a second patient-specific atrial model reconstructed from in vivo LGE-MRI data from a patient with PsAF.

In previous work, one of the inventors carried out pilot studies to demonstrate the feasibility of developing patient-specific atrial models and conducting realistic simulations of PsAF to obtain predictions of optimal ablation targets. Those results include the construction of four atrial models (two are shown in FIGS. 16A and 16B) from pre-ablation in vivo LGE-MRI scans of PsAF patient hearts provided by Dr. Hubert Cochet from the University of Bordeaux. LGE-MRI has been shown to differentiate fibrotic from non-fibrotic myocardium. [30] To create these models, we used a preliminary version of the high-throughput atrial model construction pipeline. This involved adaptation and extension of tools previously developed in Professor Trayanova's lab for ventricular model assembly. [46] These models incorporate realistic atrial fiber orientations to ensure accurate representation of anisotropic wavefront propagation. Inter-regional heterogeneities in cell- and tissue-level electrophysiological properties within fibrotic and non-fibrotic regions are also included. Notably, these are the first detailed reconstructions of bi-atrial geometry with realistic representation of patient-specific fibrosis spatial patterns.

FIGS. 16A and 16B show patient-specific atrial models reconstructed from in vivo LGE-MRI data from patients with PsAF. Gray and green represent non-fibrotic and fibrotic myocardium, respectively; lighter and darker colors represent left and right atria (LA and RA), respectively. Zoomed-in panels show activation patterns (arrows) maintained by persistent reentrant sources near fibrosis clusters during simulated PsAF; gold spheres show the dynamic (i.e., varying over time) locations of the persistent phase singularities.

Stimulation with a clinically relevant rapid pacing protocol [38] resulted in PsAF induction in all four models, consistent with the clinical records for these patients. Organizing centers were identified via phase-space analysis; [47] reentrant sources (i.e., phase singularities) lasting ≥2 seconds were classified as persistent (see inset panels of FIGS. 16A and 16B). During simulated PsAF in each model, the dynamic (i.e., varying over time) locations of the persistent phase singularities were confined to contiguous regions. Among all cases, the maximum extent of such regions of persistent phase singularity meander was ≈2 cm. The confined regions of persistent phase singularity meander encompassed patchy intermingling of non-fibrotic (gray) and fibrotic tissue (green). We also conducted ablation simulations in all four patient-specific models. In each case, the persistent phase singularity meander region was deemed to be the ablation lesion and was modeled as inexcitable. This process rendered PsAF non-inducible in all four models, including the example shown in FIG. 17. FIG. 17 shows simulated ablation (purple) of the confined region within which persistent phase singularities (gold) meandered. As shown in the inset, PsAF could no longer be induced by the pacing protocol applied in FIG. 16A. These findings show that the dynamic locations of persistent phase singularities are the optimal PsAF ablation targets.

To demonstrate that it is the patient-specific distribution of fibrosis that determines the locations of the persistent reentrant sources (and thus the optimal targets of ablation), each simulation was repeated with ±10% $I_{K1}$ (to test the effect of APD variation) and ±10% electrical coupling (to test the effect of conduction velocity variation). These changes led to slight variation in PsAF dynamics, but the persistent organizing centers of reentrant activity meandered in nearly identical regions. This suggests that for the purposes of the proposed simulation-based predictions of optimal ablation targets, average parameter values based on typical human characteristics are appropriate for representing cell- and tissue-level electrophysiology in patient-specific models, since the dynamic locations of the PsAF-perpetuating persistent phase singularities are determined by the fibrosis pattern only. Further preliminary results were obtained to quantitatively characterize the fibrosis distribution in each model, determining the (1) density, (2) aggregation (clustering), [48] and (3) disorganization (entropy) of individual fibrosis spatial patterns. [49] FIG. 18A shows spatial metrics of fibrosis distribution were higher within regions of persistent phase singularity dynamic locations than in the atria as a whole (*=p<0.01). FIG. 18B shows a map of regions where all metric values were >0.6 (red), dynamic locations of persistent phase singularities (gold), and fibrosis (black). Within regions of persistent phase singularity meander, fibrosis metrics were significantly different from those in the rest of the atria (red vs. gray boxes, FIG. 18A). Regions where phase singularities persisted had values >0.6 for all three fibrosis metrics. In all four models, the amount of tissue in the entire atria with this particular property (red areas in FIG. 18B) was small compared to the amount of fibrosis by volume (5.23% and 25.5%, respectively, for the case shown here); this suggests that in individual hearts, only a small sub-volume of all fibrotic tissue has the specific spatial pattern that favors PsAF reentrant source perpetuation.

The above findings indicate that (1) phase singularities located in these regions underlie PsAF-perpetuating reentrant activity; (2) ablation of these regions renders PsAF non-inducible; (3) these locations are predominantly determined by the individual fibrosis distribution and are insensitive to changes in the electrophysiological properties of atrial tissue within the range of physiological values; and, (4) within these regions, there is a distinct and quantifiable fibrosis spatial pattern that promotes the localization of persistent phase singularities.

Research Methodology—Quantitative Characterization of Fibrosis Spatial Patterns

Figures 19A, 19B, 19C, 19D:
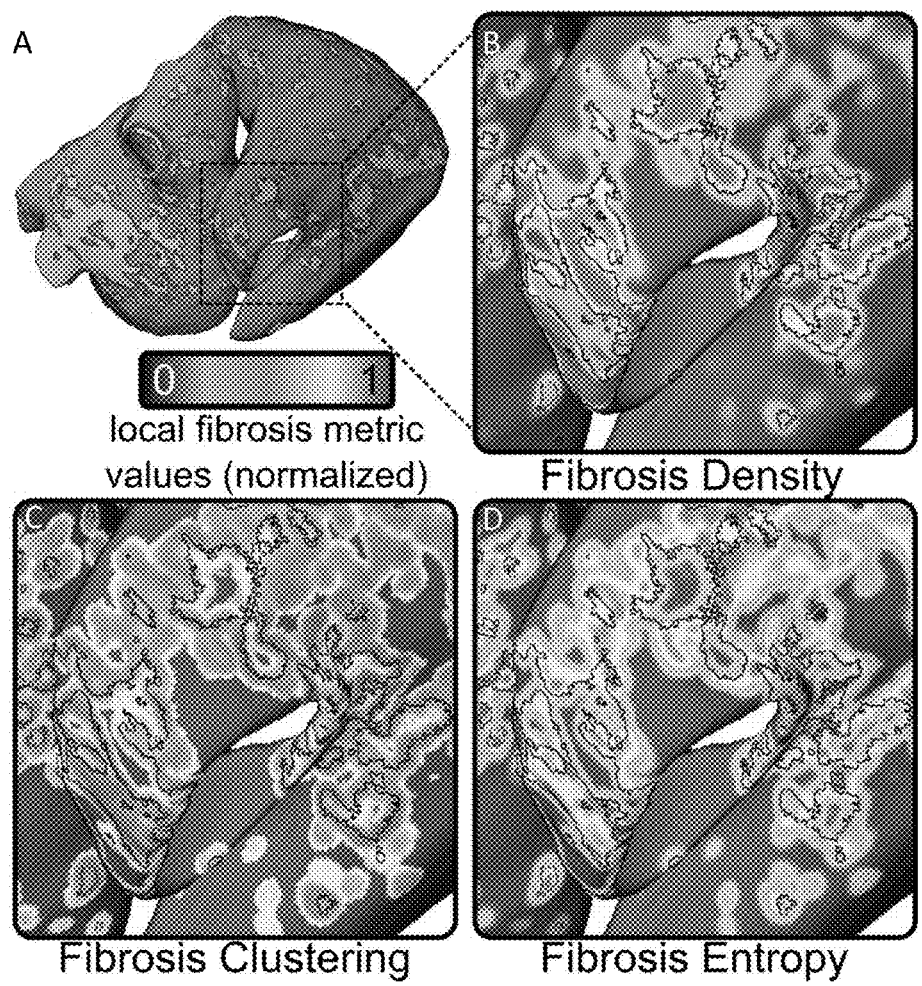
FIG. 19A shows distribution of fibrotic (green) and non-fibrotic (grey) regions within one atrial model.
FIG. 19B shows a map of normalized local fibrosis density (same as FD above)
FIG. 19C shows a map of normalized local fibrosis clustering.
FIG. 19D shows a map of normalized local fibrosis entropy (same as FE above)

The properties of the individual fibrosis distribution in each of the 28 patient-specific atrial models is characterized by calculating a set of spatial metrics. At every atrial point, breadth-first search technique is used to build a list of connected tissue elements in the volume within a 2.5 mm radius. Then, metric values local to each point for the surrounding tissue region are computed as follows: fibrosis density, via the proportion of fibrotic elements by volume; fibrosis clustering, via normalized Moran's I, [48] a measure of spatial autocorrelation, which ranges from most diffuse (0) to most aggregated (1); and fibrosis entropy, via normalized Shannon entropy, [49] which ranges from least (0) to most (1) disorganized. For one patient-specific model, FIG. 19 shows a preliminary result: the comparison of these three metrics with the underlying fibrosis spatial pattern. The same methodology was used to generate preliminary findings presented in FIGS. 18A and 18B.

References—Example 2

[1] Andrade J, Khairy P, Dobrev D, Nattel S. The clinical profile and pathophysiology of atrial fibrillation: relationships among clinical features, epidemiology, and mechanisms. Circ Res. 2014; 114(9):1453-68.

[2] Go A S, Hylek E M, Phillips K A, Chang Y, Henault L E, Selby J V, et al. Prevalence of diagnosed atrial fibrillation in adults: national implications for rhythm management and stroke prevention: the AnTicoagulation and Risk Factors in Atrial Fibrillation (ATRIA) Study. JAMA. 2001; 285(18):2370-5.

[3] Dorian P, Jung W, Newman D, Paquette M, Wood K, Ayers G M, et al. The impairment of health-related quality of life in patients with intermittent atrial fibrillation: implications for the assessment of investigational therapy. J Am Coll Cardiol. 2000; 36(4): 1303-9.

[4] Kalantarian S, Stern T A, Mansour M, Ruskin J N. Cognitive impairment associated with atrial fibrillation: a meta-analysis. Ann Intern Med. 2013; 158(5 Pt 1):338-46.

[5] Stewart S, Murphy N F, Walker A, McGuire A, McMurray J J. Cost of an emerging epidemic: an economic analysis of atrial fibrillation in the U K. Heart. 2004; 90(3):286-92.

[6] Woods C E, Olgin J. Atrial fibrillation therapy now and in the future: drugs, biologicals, and ablation. Circ Res. 2014; 114(9):1532-46.

[7] Brooks A G, Stiles M K, Laborderie J, Lau D H, Kuklik P, Shipp N J, et al. Outcomes of long-standing persistent atrial fibrillation ablation: a systematic review. Heart Rhythm. 2010; 7(6):835-46.

[8] Camm A J, Al-Khatib S M, Calkins H, Halperin J L, Kirchhof P, Lip G Y, et al. A proposal for new clinical concepts in the management of atrial fibrillation. Am Heart J. 2012; 164(3):292-302 e1.
[9] Nattel S, Guasch E, Savelieva I, Cosio F G, Valverde I, Halperin J L, et al. Early management of atrial fibrillation to prevent cardiovascular complications. Eur Heart J. 2014; 35(22): 1448-56.
[10] Yue L, Xie J, Nattel S. Molecular determinants of cardiac fibroblast electrical function and therapeutic implications for atrial fibrillation. Cardiovasc Res. 2011; 89(4):744-53.
[11] Burstein B, Nattel S. Atrial fibrosis: mechanisms and clinical relevance in atrial fibrillation. J Am Coll Cardiol. 2008; 51(8):802-9.
[12] Platonov P G, Mitrofanova L B, Orshanskaya V, Ho S Y. Structural abnormalities in atrial walls are associated with presence and persistency of atrial fibrillation but not with age. J Am Coll Cardiol. 2011; 58(21):2225-32.
[13] Avitall B, Bi J, Mykytsey A, Chicos A. Atrial and ventricular fibrosis induced by atrial fibrillation: evidence to support early rhythm control. Heart Rhythm. 2008; 5(6):839-45.
[14] Burstein B, Qi X Y, Yeh Y H, Calderone A, Nattel S. Atrial cardiomyocyte tachycardia alters cardiac fibroblast function: a novel consideration in atrial remodeling. Cardiovasc Res. 2007; 76(3):442-52.
[15] Xu J, Cui G, Esmailian F, Plunkett M, Marelli D, Ardehali A, et al. Atrial extracellular matrix remodeling and the maintenance of atrial fibrillation. Circulation. 2004; 109(3):363-8.
[16] Rohr S. Myofibroblasts in diseased hearts: new players in cardiac arrhythmias? Heart Rhythm. 2009; 6(6):848-56.
[17] Kakkar R, Lee R T. Intramyocardial fibroblast myocyte communication. Circ Res. 2010; 106(1):47-57.
[18] He X, Gao X, Peng L, Wang S, Zhu Y, Ma H, et al. Atrial fibrillation induces myocardial fibrosis through angiotensin II type 1 receptor-specific Arkadia-mediated downregulation of Smad7. Circ Res. 2011; 108(2):164-75.
[19] Heijman J, Voigt N, Nattel S, Dobrev D. Cellular and molecular electrophysiology of atrial fibrillation initiation, maintenance, and progression. Circ Res. 2014; 114(9): 1483-99.
[20] Kostin S, Klein G, Szalay Z, Hein S, Bauer E P, Schaper J. Structural correlate of atrial fibrillation in human patients. Cardiovasc Res. 2002; 54(2):361-79.
[21] Burstein B, Comtois P, Michael G, Nishida K, Villeneuve L, Yeh Y H, et al. Changes in connexin expression and the atrial fibrillation substrate in congestive heart failure. Circ Res. 2009; 105(12):1213-22.
[22] Li D, Fareh S, Leung T K, Nattel S. Promotion of atrial fibrillation by heart failure in dogs: atrial remodeling of a different sort. Circulation. 1999; 100(1):87-95.
[23] Nattel S, Li D, Yue L. Basic mechanisms of atrial fibrillation—very new insights into very old ideas. Annu Rev Physiol. 2000; 62:51-77.
[24] Pedrotty D M, Klinger R Y, Kirkton R D, Bursac N. Cardiac fibroblast paracrine factors alter impulse conduction and ion channel expression of neonatal rat cardiomyocytes. Cardiovasc Res. 2009; 83(4):688-97.
[25] Ramos-Mondragon R, Vega A V, Avila G. Long-term modulation of Na+ and K+ channels by TGF-beta1 in neonatal rat cardiac myocytes. Pflugers Arch. 2011; 461(2):235-47.
[26] Spach M S, Dolber P C, Heidlage J F. Interaction of inhomogeneities of repolarization with anisotropic propagation in dog atria. A mechanism for both preventing and initiating reentry. Circ Res. 1989; 65(6):1612-31.
[27] Tanaka K, Zlochiver S, Vikstrom K L, Yamazaki M, Moreno J, Klos M, et al. Spatial distribution of fibrosis governs fibrillation wave dynamics in the posterior left atrium during heart failure. Circ Res. 2007; 101(8):839-47.
[28] Krogh-Madsen T, Abbott G W, Christini D J. Effects of electrical and structural remodeling on atrial fibrillation maintenance: a simulation study. PLoS Comput Biol. 2012; 8(2):1002390.
[29] Kottkamp H. Human atrial fibrillation substrate: towards a specific fibrotic atrial cardiomyopathy. Eur Heart J. 2013; 34(35):2731-8.
[30] Oakes R S, Badger T J, Kholmovski E G, Akoum N, Burgon N S, Fish E N, et al. Detection and quantification of left atrial structural remodeling with delayed-enhancement magnetic resonance imaging in patients with atrial fibrillation. Circulation. 2009; 119(13):1758-67.
[31] Mahnkopf C, Badger T J, Burgon N S, Daccarett M, Haslam T S, Badger C T, et al. Evaluation of the left atrial substrate in patients with lone atrial fibrillation using delayed-enhanced MRI: implications for disease progression and response to catheter ablation. Heart Rhythm. 2010; 7(10):1475-81.
[32] McGann C, Akoum N, Patel A, Kholmovski E, Revelo P, Damal K, et al. Atrial fibrillation ablation outcome is predicted by left atrial remodeling on MRI. Circ Arrhythm Electrophysiol. 2014; 7(1):23-30.
[33] Marrouche N F, Wilber D, Hindricks G, Jais P, Akoum N, Marchlinski F, et al. Association of atrial tissue fibrosis identified by delayed enhancement MRI and atrial fibrillation catheter ablation: the DECAAF study. JAMA. 2014; 311(5):498-506.
[34] his P, Hocini M, Hsu L-F, Sanders P, Scavee C, Weerasooriya R, et al. Technique and results of linear ablation at the mitral isthmus. Circulation. 2004; 110: 2996-3002.
[35] Haïssaguerre M, Hocini M, Sanders P, Sacher F, Rotter M, Takahashi Y, et al. Catheter ablation of long-lasting persistent atrial fibrillation: clinical outcome and mechanisms of subsequent arrhythmias. J Cardiovasc Electrophysiol. 2005; 16:1138-47.
[36] Willems S, Klemm H, Rostock T, Brandstrup B, Ventura R, Steven D, et al. Substrate modification combined with pulmonary vein isolation improves outcome of catheter ablation in patients with persistent atrial fibrillation: a prospective randomized comparison. Eur Heart J. 2006; 27:2871-8.
[37] Pak H-N, Oh Y S, Lim H E, Kim Y-H, Hwang C. Comparison of voltage map-guided left atrial anterior wall ablation versus left lateral mitral isthmus ablation in patients with persistent atrial fibrillation. Heart Rhythm. 2011; 8:199-206.
[38] Narayan S M, Krummen D E, Rappel W J. Clinical mapping approach to diagnose electrical rotors and focal impulse sources for human atrial fibrillation. J Cardiovasc Electrophysiol. 2012; 23(5):447-54.
[39] Narayan S M, Shivkumar K, Krummen D E, Miller J M, Rappel W-J. Panoramic electrophysiological mapping but not electrogram morphology identifies stable sources for human atrial fibrillation: stable atrial fibrillation rotors and focal sources relate poorly to fractionated electrograms. Circulation Arrhythmia and electrophysiology. 2013; 6:58-67.
[40] Narayan S M, Baykaner T, Clopton P, Schricker A, Lalani G G, Krummen D E, et al. Ablation of rotor and focal sources reduces late recurrence of atrial fibrillation compared with trigger ablation alone: extended follow-up of the CONFIRM trial (Conventional Ablation for Atrial Fibrillation With or Without Focal Impulse and Rotor Modulation). J Am Coll Cardiol. 2014; 63(17):1761-8.

[41] Nademanee K, McKenzie J, Kosar E, Schwab M, Sunsaneewitayakul B, Vasavakul T, et al. A new approach for catheter ablation of atrial fibrillation: mapping of the electrophysiologic substrate. J Am Coll Cardiol. 2004; 43:2044-53.

[42] Verma A, Mantovan R, Made L, De Martino G, Chen J, Morillo Ca, et al. Substrate and Trigger Ablation for Reduction of Atrial Fibrillation (STAR AF): a randomized, multicentre, international trial. Eur Heart J. 2010; 31:1344-56.

[43] Dixit S, Marchlinski F E, Lin D, Callans D J, Bala R, Riley M P, et al. Randomized ablation strategies for the treatment of persistent atrial fibrillation: RASTA study. Circulation Arrhythmia and electrophysiology. 2012; 5:287-94.

[44] Letsas K P, Efremidis M, Charalampous C, Tsikrikas S, Sideris A. Current Ablation Strategies for Persistent and Long-Standing Persistent Atrial Fibrillation. Cardiol Res Pract. 2011; 2011.

[45] Patel A R, Shah M. Intra-Atrial Re-entrant Tachycardia Substrate Mapping Using the Ensite NavX™ Navigation and Visualization Technology in Post-Surgical Congenital Heart Disease Patients: Assessment of Automated Voltage Maps. J Innovat Card Rhythm Manag. 2012; December: 1055-61.

[46] Vadakkumpadan F, Rantner L J, Tice B, Boyle P, Prassl A J, Vigmond E, et al. Image-based models of cardiac structure with applications in arrhythmia and defibrillation studies. J Electrocardiol. 2009; 42(2):157 e1-10.

[47] Iyer A N, Gray R A. An experimentalist's approach to accurate localization of phase singularities during reentry. Ann Biomed Eng. 2001; 29(1):47-59.

[48] Moran P A. Notes on continuous stochastic phenomena. Biometrika. 1950; 37(1-2): 17-23.

[49] Shannon C E. A mathematical theory of communication. Bell System Technical Journal, The. 1948; 27(3): 379-423.

Example 3: Prevalence of Regions with Highly Intermingled Fibrotic and Non-Fibrotic Tissue is a Better Predictor of Arrhythmia Inducibility than Total Fibrosis Burden: Analysis of Patient-Specific Models of Persistent Atrial Fibrillation Atrial fibrosis burden (FB) is linked to higher risk of persistent atrial fibrillation (PsAF). We have shown that PsAF reentrant sources are harbored near edges of fibrotic regions, where there is extensive intermingling with non-fibrotic tissue. However, it has heretofore been unknown if the prevalence of such regions is correlated with PsAF inducibility and, if so, whether it better predicts inducibility compared to FB. We used patient-specific atrial models to address this question.

Figures 20A, 20B, 20C, 20D, 20E:
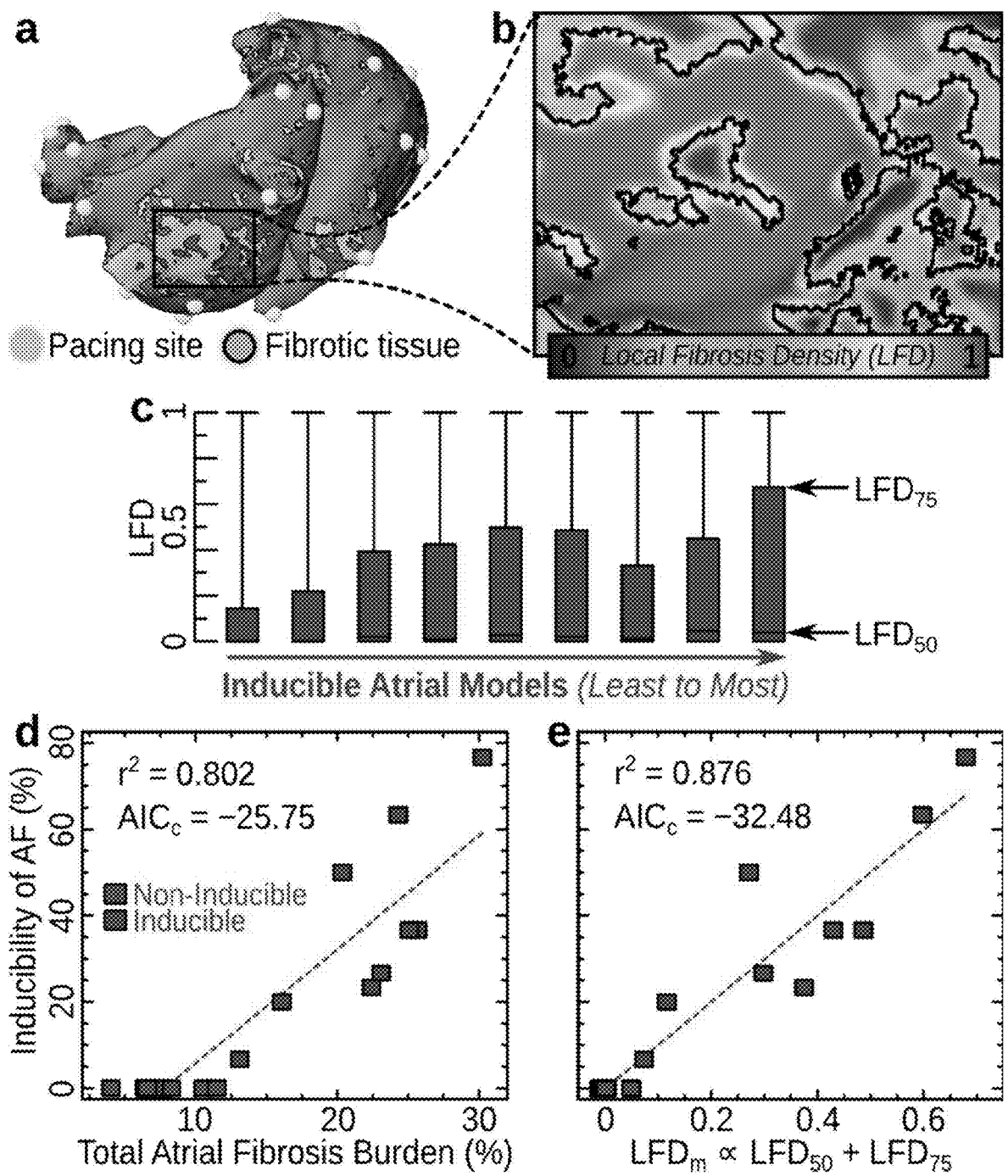
FIG. 20A shows the 30 sites where rapid pacing was applied to atrial models built from LGE-MRI scans.
FIG. 20B shows the local fibrosis density (LFD; same as FD above) in the region indicated in FIG. 20A.
FIG. 20C shows fibrosis density for nine inducible atrial models, organized in order of increasing inducibility to AF.
FIG. 20D shows inducibility to AF versus total atrial fibrosis burden.
FIG. 20E shows inducibility to AF versus a linear combination of median & upper quartile FD values, LFD50 & LFD75.

Atrial models were built from LGE-MRI scans of 18 PsAF patients. Rapid pacing was applied at the 30 sites indicated in FIG. 20A. The inducibility rate was the proportion of sites that induced PsAF. Fibrosis was quantified via the proportion of LGE tissue by volume, either in the whole atria (FB) or in the volume within 1.5 mm of each point (termed local fibrosis density, LFD; FIG. 20B). Aggregate LFD properties (median & upper quartile values, LFD50 & LFD75) estimated the prevalence of regions with highly intermingled fibrotic and non-fibrotic tissue.

Non-inducible models had low FB ($\leq 11\%$) and LFD75 ($\leq 0.1$). In remaining models, higher inducibility was associated with increased FB (13-30%) and LFD (LFD75=0.14-0.67; FIG. 20C). Inducibility was correlated both with FB ($r2=0.748$; FIG. 20D) and with LFDm, a linear combination of LFD50 and LFD75 ($r2=0.876$; FIG. 20E). Akaike information criterion (AICc) analysis showed that LFDm had more predictive power than FB (likelihood of FB producing better predictions than $LFD_m$ was ~3%).

In conclusion, personalized simulations show that PsAF inducibility is better predicted by LFDm than by FB. Fibrosis spatial pattern analysis could be a novel avenue for PsAF risk stratification.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for providing an atrial fibrillation (AF) ablation treatment plan, comprising:
    receiving imaging data for at least a portion of an atrial region of a subject's heart;
    processing said imaging data to characterize tissue as one of fibrotic tissue or non-fibrotic tissue;
    calculating a metric of spatial distribution of at least a portion of said tissue characterized as fibrotic tissue from said processing said imaging data;
    identifying a cardiac tissue ablation target based on said metric; and
    providing an AF treatment plan that includes said cardiac tissue ablation target as at least a portion of said AF treatment plan,
    wherein said metric of spatial distribution is calculated for each of a plurality of subvolumes of said atrial regions of said subject's heart; and
    wherein said plurality of subvolumes are between 1.3 mm and 1.7 mm in radius.

2. The method of claim 1, wherein said receiving imaging data is receiving at least one of MRI, CT or PET imaging data.

3. The method of claim 1, wherein said receiving imaging data is receiving late gadolinium enhancement magnetic resonance (LGE-MRI) data.

4. The method of claim 1, further comprising identifying a plurality of cardiac tissue ablation targets based on said metric,
    wherein said AF treatment plan further includes said plurality of cardiac tissue ablation targets.

5. The method of claim 1, further comprising calculating a plurality of metrics of spatial distribution of tissue characterized as fibrotic tissue from said processing said imaging data.

6. The method of claim 1, wherein said calculating a metric comprises calculating said metric for a portion of said tissue characterized as fibrotic tissue having a degree of fibrosis that falls within a predetermined range.

7. A method for providing an atrial fibrillation (AF) ablation treatment plan, comprising:
receiving imaging data for at least a portion of an atrial region of a subject's heart;
processing said imaging data to characterize tissue as one of fibrotic tissue or non-fibrotic tissue;
calculating a metric of spatial distribution of at least a portion of said tissue characterized as fibrotic tissue from said processing said imaging data;
identifying a cardiac tissue ablation target based on said metric;
providing an AF treatment plan that includes said cardiac tissue ablation target as at least a portion of said AF treatment plan; and
calculating a plurality of metrics of spatial distribution of tissue characterized as fibrotic tissue from said processing said imaging data,
wherein said plurality of metrics include at least density, clustering and complexity metrics.

8. A method for providing a risk assessment for atrial fibrillation (AF) and related health risks, as well as recurrence of atrial arrhythmia after ablation, comprising:
receiving imaging data for at least a portion of an atrial region of a subject's heart;
processing said imaging data to characterize tissue as one of fibrotic tissue or non-fibrotic tissue;
calculating a metric of spatial distribution of at least a portion of said tissue characterized as fibrotic tissue from said processing said imaging data for a plurality of localized regions within said portion of said atrial region of said subject's heart;
identifying a risk of at least one of developing atrial fibrillation, worsening atrial fibrillation, recurrence of atrial arrhythmias and fibrillation after ablation treatment, heart failure, or stroke based said metric of spatial distribution calculated for said plurality of localized regions,
wherein said metric of spatial distribution is calculated for each of a plurality of subvolumes of said atrial regions of said subject's heart; and
wherein said plurality of subvolumes are between 1.3 mm and 1.7 mm in radius.

9. The method of claim 8, wherein said receiving imaging data is receiving at least one of MRI, CT or PET imaging data.

10. The method of claim 8, wherein said receiving imaging data is receiving late gadolinium enhancement magnetic resonance (LGE-MRI) data.

11. A non-transitory computer-readable medium comprising computer-executable code for providing an atrial fibrillation (AF) ablation treatment plan, said computer-executable code comprising instructions that, when executed by the computer, causes the computer to:
receive imaging data for at least a portion of an atrial region of a subject's heart;
process said imaging data to characterize tissue as one of fibrotic tissue or non-fibrotic tissue;
calculate a metric of spatial distribution of at least a portion of said tissue characterized as fibrotic tissue from said processing said imaging data;
identify a cardiac tissue ablation target based on said metric; and
provide an AF treatment plan that includes said cardiac tissue ablation target as at least a portion of said AF treatment plan,
wherein said metric of spatial distribution is calculated for each of a plurality of subvolumes of said atrial regions of said subject's heart; and
wherein said plurality of subvolumes are between 1.3 mm and 1.7 mm in radius.

12. A non-transitory computer-readable medium comprising computer-executable code for providing a risk assessment for atrial fibrillation (AF) and related health risks, as well as recurrence of atrial arrhythmia after ablation when executed by the computer, causes the computer to:
receive imaging data for at least a portion of an atrial region of a subject's heart;
process said imaging data to characterize tissue as one of fibrotic tissue or non-fibrotic tissue;
calculate a metric of spatial distribution of at least a portion of said tissue characterized as fibrotic tissue from said processing said imaging data for a plurality of localized regions within said portion of said atrial region of said subject's heart;
identify a risk of at least one of developing atrial fibrillation, worsening atrial fibrillation, recurrence of atrial arrhythmias and fibrillation after ablation treatment, heart failure, or stroke based said metric of spatial distribution calculated for said plurality of localized regions,
wherein said metric of spatial distribution is calculated for each of a plurality of subvolumes of said atrial regions of said subject's heart; and
wherein said plurality of subvolumes are between 1.3 mm and 1.7 mm in radius.

13. A medical imaging system comprising a data processor configured to:
receive imaging data for at least a portion of an atrial region of a subject's heart;
process said imaging data to characterize tissue as one of fibrotic tissue or non-fibrotic tissue;
calculate a metric of spatial distribution of at least a portion of said tissue characterized as fibrotic tissue from said processing said imaging data for a plurality of localized regions within said portion of said atrial region of said subject's heart; and
provide at least one of a map based on said metric, at least one ablation target based on said metric, or a risk assessment for at least one of developing atrial fibrillation, worsening atrial fibrillation, recurrent atrial fibrillation, heart failure, or stroke based said metric,
wherein said metric of spatial distribution is calculated for each of a plurality of subvolumes of said atrial regions of said subject's heart; and
wherein said plurality of subvolumes are between 1.3 mm and 1.7 mm in radius.

14. An ablation system configured to receive data from the medical imaging system of claim 13 to provide guidance to a user for electro-anatomical mapping and/or ablation.

15. A method for providing a risk assessment for atrial fibrillation (AF) and related health risks, as well as recurrence of atrial arrhythmia after ablation, comprising:
receiving imaging data for at least a portion of an atrial region of a subject's heart;
processing said imaging data to characterize tissue as one of fibrotic tissue or non-fibrotic tissue;
calculating a metric of spatial distribution of at least a portion of said tissue characterized as fibrotic tissue from said processing said imaging data for a plurality of localized regions within said portion of said atrial region of said subject's heart;

identifying a risk of at least one of developing atrial fibrillation, worsening atrial fibrillation, recurrence of atrial arrhythmias and fibrillation after ablation treatment, heart failure, or stroke based said metric of spatial distribution calculated for said plurality of localized regions; and calculating a plurality of metrics of spatial distribution of tissue characterized as fibrotic tissue from said processing said imaging data, wherein said plurality of metrics include at least density, clustering and complexity metrics.

16. A non-transitory computer-readable medium comprising computer-executable code for providing an atrial fibrillation (AF) ablation treatment plan, said computer-executable code comprising instructions that, when executed by the computer, causes the computer to:

receive imaging data for at least a portion of an atrial region of a subject's heart;

process said imaging data to characterize tissue as one of fibrotic tissue or non-fibrotic tissue;

calculate a metric of spatial distribution of at least a portion of said tissue characterized as fibrotic tissue from said processing said imaging data;

identify a cardiac tissue ablation target based on said metric; and provide an AF treatment plan that includes said cardiac tissue ablation target as at least a portion of said AF treatment plan; and calculate a plurality of metrics of spatial distribution of tissue characterized as fibrotic tissue from said processing said imaging data, wherein said plurality of metrics include at least density, clustering and complexity metrics.

17. A non-transitory computer-readable medium comprising computer-executable code for providing a risk assessment for atrial fibrillation (AF) and related health risks, as well as recurrence of atrial arrhythmia after ablation when executed by the computer, causes the computer to:

receive imaging data for at least a portion of an atrial region of a subject's heart;

process said imaging data to characterize tissue as one of fibrotic tissue or non-fibrotic tissue;

calculate a metric of spatial distribution of at least a portion of said tissue characterized as fibrotic tissue from said processing said imaging data for a plurality of localized regions within said portion of said atrial region of said subject's heart;

identify a risk of at least one of developing atrial fibrillation, worsening atrial fibrillation, recurrence of atrial arrhythmias and fibrillation after ablation treatment, heart failure, or stroke based said metric of spatial distribution calculated for said plurality of localized regions; and calculate a plurality of metrics of spatial distribution of tissue characterized as fibrotic tissue from said processing said imaging data, wherein said plurality of metrics include at least density, clustering and complexity metrics.

18. A medical imaging system comprising a data processor configured to:

receive imaging data for at least a portion of an atrial region of a subject's heart;

process said imaging data to characterize tissue as one of fibrotic tissue or non-fibrotic tissue;

calculate a metric of spatial distribution of at least a portion of said tissue characterized as fibrotic tissue from said processing said imaging data for a plurality of localized regions within said portion of said atrial region of said subject's heart; and provide at least one of a map based on said metric, at least one ablation target based on said metric, or a risk assessment for at least one of developing atrial fibrillation, worsening atrial fibrillation, recurrent atrial fibrillation, heart failure, or stroke based said metric; and calculate a plurality of metrics of spatial distribution of tissue characterized as fibrotic tissue from said processing said imaging data, wherein said plurality of metrics include at least density, clustering and complexity metrics.

* * * * *